United States Patent [19]

Mookherjee et al.

[11] 4,000,050
[45] Dec. 28, 1976

[54] PHOTOCHEMICAL PREPARATION OF POLYCYCLOALKYL OXYALKANES AND OXYALKENES

[75] Inventors: Braja Dulal Mookherjee, Matawan; Venkatesh Kamath, Red Bank; Ramanlal Ranchodji Patel, Cranbury, all of N.J.; Edward J. Shuster, Brooklyn, N.Y.

[73] Assignee: International Flavors & Fragrances Inc., New York, N.Y.

[22] Filed: Feb. 19, 1975

[21] Appl. No.: 551,030

[52] U.S. Cl. .......................... 204/162 R; 252/522; 260/617 F
[51] Int. Cl.² ............................................ B01J 1/10
[58] Field of Search ............... 204/162 R; 252/522; 260/617 F

[56] References Cited

UNITED STATES PATENTS

| | | | |
|---|---|---|---|
| 3,433,839 | 3/1969 | Moroe et al. | 204/162 R X |
| 3,505,412 | 4/1970 | Klein | 204/162 R |
| 3,616,372 | 10/1971 | Kropp | 204/162 R |
| 3,723,271 | 3/1973 | Schulte-Elte | 204/162 R |

OTHER PUBLICATIONS

Colonge et al., *Bull. Soc. Chim. France*, 1966, pp. 374–376.
Foote, *Accounts of Chem. Research*, 1, pp. 104–110 (1968).
Hodgson et al., *Chem. Abs.*, 77, p. 471, Abs. No. 140311 (1972).

*Primary Examiner*—Edward A. Miller
*Attorney, Agent, or Firm*—Arthur L. Liberman; Harold Haidt

[57] ABSTRACT

Processes and compositions are described for altering the aroma of consumable products including perfumes, perfume compositions and perfumed articles utilizing as the essential ingredient one or more of the polycycloalkyl oxyalkanes and/or oxyalkenes (broadly hereinafter referred to as polycycloalkyl oxyhydrocarbons) having the generic formula:

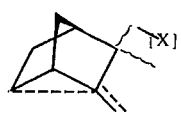

the polycyclic moiety being bicyclic or tricyclic, wherein X is one of the moieties:

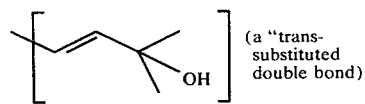

(a "trans-substituted double bond)

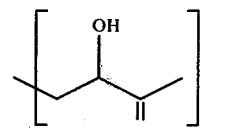

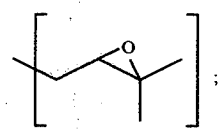

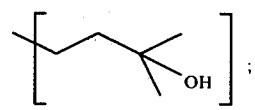

provided that the polycyclic moiety is tricyclic only when X contains an epoxide moiety; and wherein one of the dashed lines is a carbon-carbon bond and each of the wavy lines is a carbon-carbon single bond, one of the carbon-carbon single bonds represented by the wavy line being epimeric with respect to the other of the carbon-carbon single bonds represented by the wavy line; and processes for preparing individual compounds or mixtures of these compounds including the steps of:

i. Subjecting one or more santalene hydrocarbons having the generic structure:

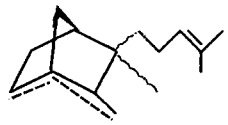

to photooxidation with oxygen, base and ultra violet light to form a mixture of compounds having the generic structures:

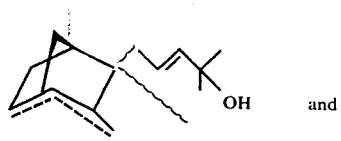

and

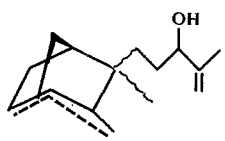

ii. Optionally fractionally distilling the resulting reaction products for utilization; or
iii. Optionally reacting α-santalene, beta-santalene, epi-beta-santalene or mixtures thereof with a peracid to produce onr or more epoxide compounds having the generic structure:

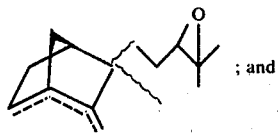; and iv. Optionally fractionally distilling the resulting reaction product(s) for utilization; and/or
v. Optionally reducing the resulting epoxide with lithium aluminum hydride to form one or more tertiary alcohols having the generic structure:

vi. Optionally fractionally distilling the thus formed tertiary alcohol(s); or
vii. Rearranging the epoxide compounds having the generic formula:

using diphenyl diselenide and sodium borohydride to form one or more allylic tertiary alcohols having the generic formula:

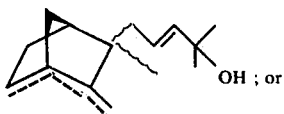; or viii. Optionally rearranging the epoxide compounds having the structure:

using aluminum isopropoxide to form allylic secondary alcohols having the generic structure:

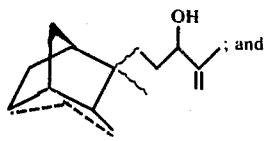; and ix. Optionally fractionally distilling the allylic secondary alcohols.

In addition the novel compounds having the generic structure:

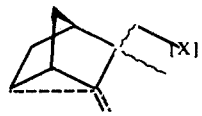

as well as the structure:

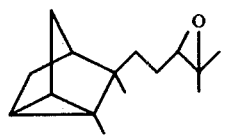

wherein X is one of the moieties:

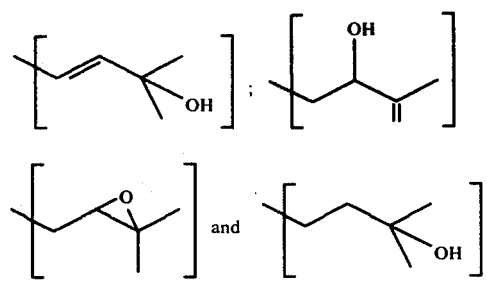

are described.

8 Claims, No Drawings

PHOTOCHEMICAL PREPARATION OF POLYCYCLOALKYL OXYALKANES AND OXYALKENES

BACKGROUND OF THE INVENTION

East Indian sandalwood oil has heretofore been available only from East Indian sandalwood trees (age-60–80 years). This oil and various individual components of the oil are highly valued perfume bases and are used in large quantities by the perfume industry. The oil, however, is expensive and is in limited and sometimes sporadic, supply. For this reason, a continuous effort has been made to synthesize the various components of sandalwood oil or similar synthetic materials which possess odors similar to the desirable woody fragrance of sandalwood oil.

Synthetic bicyclo(2.2.1) heptanes and the processes for preparing these compounds represent a portion of an extensive scientific effort to prepare compounds having the valuable characteristics of sandalwood. Other processes and compounds relating to the synthesis of synthetic sandalwood oil components are described in the following U.S. Patents:

i. Perfume Compounds And Process For Preparing Same U.S. Pat. No. 3,673,261 issued June 27, 1972: Compounds:

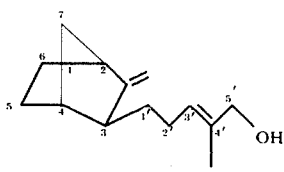

2-methylene-3-exo(trans-4'-methyl-5'-hydroxypent-3'-enyl)bicyclo[2.2.1]heptane trans-3-Normethyl-β-santalol

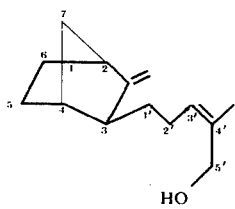

2-methylene-3-exo(cis-4'-methyl-5'-hydroxypent-3'-enyl)bicyclo[2.2.1]heptane cis-3-normethyl-β-santalol

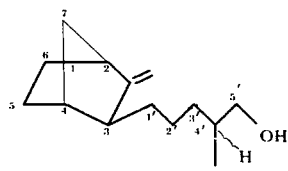

2-methylene-3-exo(4'-methyl-5'-hydroxypentyl)bicyclo[2.2.1]heptane 3-normethyldihydro-β-santalol ii. Dihydro-beta-santalol and Processes For Preparing Dihydro-beta-Santalol From 3-Endo-Methyl-3-Exo(4'-Methyl-5'-Hydroxyphenyl) Norcamphor — U.S. Pat. No. 3,673,263 issued June 27, 1972:

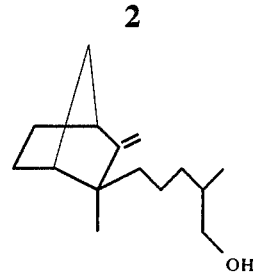

dihydro-beta-santalol iii. Process For Preparing Beta-Santalol From 3-Methylnorcamphor — U.S. Pat. No. 3,662,008 issued May 9, 1972:

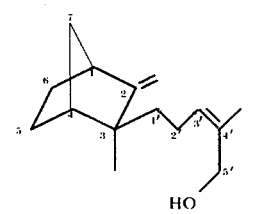

endo-3-methyl-exo-3(cis-5'-hydroxy-4'-methylpent-3'-enyl)-2-methylenebicyclo-(2.2.1) heptane

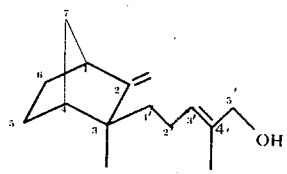

endo-3-methyl-exo-3(trans-5'-hydroxy-4'-methylpent-3'-enyl)-2-methylenebicyclo(2.2.1) heptane iv. Process For Preparing Dihydro-Beta-Santalol From 3-Endo-Methyl-3-Exo(4'-Methyl-5'-Hydroxypentyl) Norcamphor — U.S. Pat. No. 3,673,266, issued June 27, 1972:

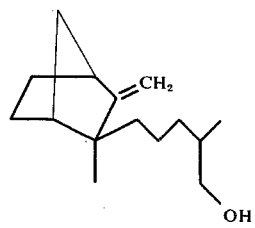

dihydro-beta-santalol

In addition, a relatively large quantity of investigative work has been carried out concerning photochemistry in the field of monoterpenes and related compounds. Thus U.S. Pat. No. 3,673,066 concerns a process for the preparation of verbenone, myrtenol, myrtenal, trans-verbenol, cis-verbenol, pinocarbeol, alpha-pinene epoxide and campholene aldehyde comprising:

I. Subjecting oil of turpentine to an intense oxidation step comprising continuously insufflating air through said oil at a temperature of about 70° C while agitating said oil and irradiating said oil with ultraviolet light in the presence of:

a. From 0.05 to 0.5 percent by weight of a promoter selected from the group consisting of organic salts and complexes of nickel, vanadium, tungsten, tantalum, niobium, rhenium, tellurium and selenium, and
b. In the presence of from 1 to 10 percent by weight of at least one catalyst selected from the group consisting of:
 1. The abietates, the levopimarates, the dextropimarates and the pinonates of cobalt, manganese and nickel; and
 2. A member selected from the group consisting of the acetylacetonates, the phthalocyanines and the terpenic acid salts of nickel, cobalt, vanadium, tungsten, tantalum, niobium and rhenium; the oxides of selenium and tellurium; the naphthenates, the oleates, and the stearates of cobalt, manganese and nickel; in the presence of from 0.05 to 0.5 percent by weight of at least one member selected from the group consisting of copper (II) salts, cesium salts and mixtures thereof;
II. Distilling off the reaction products having a boiling point of about 75° C at 10 mm Hg; and
III. Rectifying the distilled reaction products collected, is disclosed.

A paper by Michel Pfau entitled "Photochemistry in the Field of Monoterpenes and Related Compounds" (The Flavour Industry, February, 1972, Page 89–103) discloses, interalia the following reaction sequence:

The compounds described and processes described and the above cited prior art do not suggest the compounds and processes of the instant invention. Indeed nothing in the prior art sets forth such strong sandalwood fragrances as the compounds of the instant invention and no process in the prior art teaches such a commercially feasible process as is set forth herein.

Thus, a complex multi-step process for producing the compound having the structure:

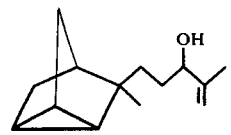

is taught by Colonge et al., Bull.Soc.Chim.France 1966, pp. 374–376 ("Synthese de Santatols") and a complex process for producing compounds having the generic structure:

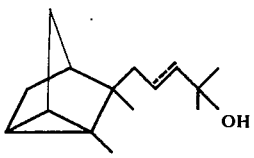

(covering only the "cis" isomer)

is taught in U.S. Pat. No. 3,390,197.

THE INVENTION

This invention relates to processes for preparing compounds having valuable sandalwood aromas useful in perfume compositions and perfumed articles, from synthetic and/or natural santalenes, specifically: alpha-santalene, beta-santalene and epi-beta-santalene. Our invention also contemplates the altering of the fra-

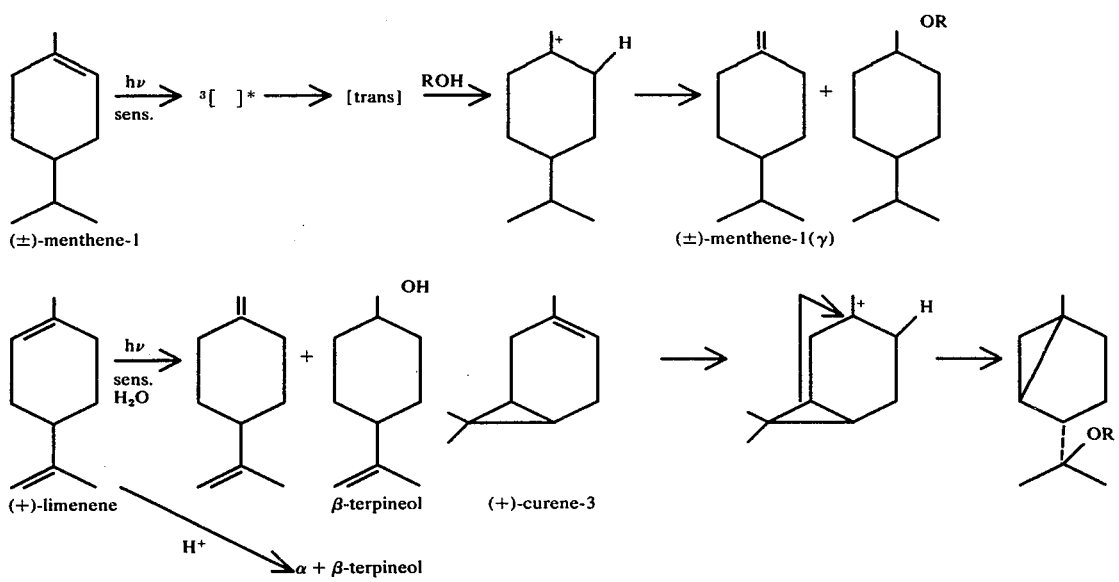

grances of such consumable materials as perfumes, perfumed formulations and perfumed articles by adding thereto a small but effective amount of at least one bicyclic or tricyclic compound of the genus having the structure:

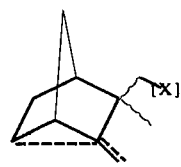

wherein X is a moiety selected from the group consisting of:

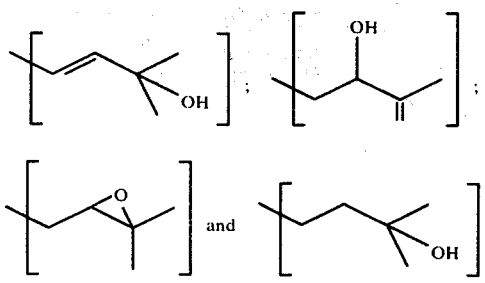

provided that the polycyclic moiety is tricyclic only when X contains an epoxide moiety, and wherein one of the dashed lines is a carbon-carbon bond and each of the wavy lines is a carbon-carbon single bond, one of the carbon-carbon single bonds represented by the wavy line being epimeric with respect to the other of the carbon-carbon single bonds represented by the wavy line.

A number of these materials are novel and these are represented by the structures:

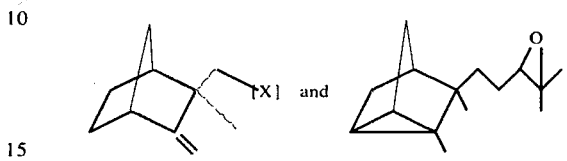

wherein X is as defined above.

Specific examples of the materials contemplated for use in our invention are as follows:

| NOMENCLATURE OF REACTION PRODUCT | STRUCTURE OF REACTION PRODUCT(S) | FRAGRANCE EVALUATIONS |
|---|---|---|
| 5-(2,3-Dimethyl tricyclo [2.2.1.0$^{2,6}$]-hept-3-yl)-2-methyl-3-penten-2-ol | | Oily, woody, sweet, pumpkin strong sandal, fruity, bready, slightly green, nutty aroma with floral, woody, slightly fatty, rosey and vetiverol-like notes. |
| 5-(2,3-Dimethyl tricyclo [2.2.1.0$^{2,6}$]-hept-3-yl)-2-methyl-pentan-2-ol | | Low keyed green, woody and "burnt match" notes. |
| 2-Methyl-5-(2-exo-methyl-3-methylene-bicyclo-[2.2.1]-hept-2-yl)-pentan-2-ol | | Green, ozoney, geranidal-like, pseudotrianone-like, sweet, woody and sandal-like notes with a "burnt match" nuance. |
| 2-Methyl-5-(2-endo-methyl-3-methylene-bicyclo-[2.2.1]-hept-2-yl)-pentan-2-ol | | Green, ozoney, geranidal-like, pseudotrianone-like note with sweet, woody and "burnt match" nuances. |
| 2-Methyl-5-(2-exo-methyl-3-methylene-bicyclo-[2.2.1]-hept-2-yl)-3-penten-2-ol | | Long lasting, woody, sandal aroma with fruity and musky-fecal undertones. This compound is the strongest of the genus of polycycloalkane alkanols and alkenols. |
| 2-Methyl-5-(2-endo-methyl-3-methylene-bicyclo-[2.2.1]-hept-2-yl)-3-penten-2-ol | | Oily, peanut-like, woody, green intense sandal aroma with a wet bark top note. |
| 2-Methyl-3-methylene alpha-(1-methylethenyl)-bicyclo-[2.2.1]-heptane-2-endo-propanol | | Oily, green, sandal, woody, peppery, piney aroma with bready, guaicwoody nuances. |

-continued

| NOMENCLATURE OF REACTION PRODUCT | STRUCTURE OF REACTION PRODUCT(S) | FRAGRANCE EVALUATIONS |
|---|---|---|
| 2-Methyl-3-methylene-alpha-(1-methylethenyl)-bicyclo-[2.2.1]-heptane-2-exo-propanol | 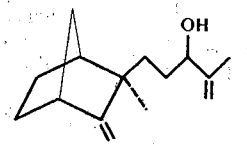 | Sweet, woody, fruity, oily, green aroma |
| Mixture of: <br><br>(i) 5-(2,3-Dimethyl tricyclo [2.2.1.0$^{2,6}$]-hept-3-yl)-2-methyl-3-penten-2-ol <br><br>(ii) 5-(2,3-Dimethyl tricyclo [2.2.1.0$^{2,6}$]-hept-3-yl)-2-methyl-pentan-2-ol <br><br>(iii) 2-Methyl-5-(2-exo-methyl-3-methylene-bicyclo-[2.2.1]-hept-2-yl)-pentan-2-ol <br><br>(iv) 2-Methyl-5-(2-endo-methyl-3-methylene-bicyclo-[2.2.1]-hept-2-yl)-pentan-2-ol <br><br>(v) 2-Methyl-5-(2-exo-methyl-3-methylene-bicyclo-[2.2.1]-hept-2-yl)-3-penten-2-ol <br><br>(vi) 5-(2,3-dimethyl tricyclo [2.2.1.0$^{2,6}$]-hept-3-yl)-alpha(1-methylethenyl)-2-propanol | Mixture Having Generic Structures <br><br>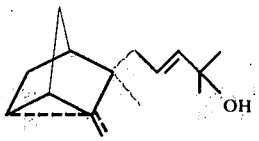 <br><br>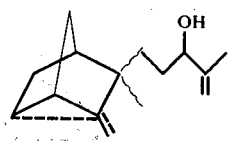 | Column chromatography fractions 15-22 have strong hay acetophenone-like notes with oily undertones; the oily nuttiness is the top note of sandalwood. Fractions 23-31 have sandal-wood resinous aromas with almond nuances. Fractions 32-38 have an intense sandal-wood-like aroma with leathery nuances. |
| 5-(2,3-Dimethyl tricyclo-[2.2.1.0$^{2,6}$]-hept-3-yl)-2-methyl-2,3-epoxypentane | 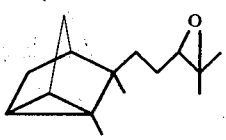 | Geranidal-like note. |
| Mixtures of: <br><br>(i) 5-(2,3-Dimethyl tricyclo-[2.2.1.0$^{2,6}$]-hept-3-yl) 2-methyl-2,3-epoxypentane <br><br>(ii) 2-Methyl-5-(2-endo-methyl-3-methylene-bicyclo-[2.2.1]-hept-2-yl)-2,3-epoxypentane |  | Green woody aroma. |
| 2-Methyl-5-(2-endo-methyl-3-methylene-bicyclo-[2.2.1]-hept-2-yl)-2,3-epoxypentane | 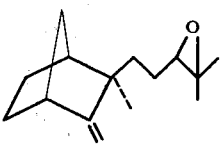 | Green woody aroma. |
| Mixture of <br><br>(i) 47% 5-(2,3-dimethyl-tricyclo [2.2.1.0$^{2,6}$]-hept-3-yl)-alpha(1-methylethenyl)-2-propanol; <br><br>(ii) 26% 2-methyl-3-methylene alpha-(1-methylethenyl)-bicyclo-[2.2.1]-heptane-2-endo-propanol; and | 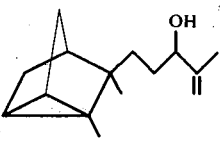 <br><br>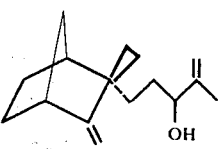 | Oily, woody with animal note reminisent of castorium with very strong sandalwood top note. |

| NOMENCLATURE OF REACTION PRODUCT | STRUCTURE OF REACTION PRODUCT(S) | FRAGRANCE EVALUATIONS |
|---|---|---|
| (iii) 26% 2-methyl-3-methylene-alpha-(1-methylethenyl)-bicyclo-[2.2.1]-heptane-2-exo-propanol | | |
| Mixture of | | |
| (i) 36% 5-(2,3-dimethyl tricyclo [2.2.1.0$^{2,6}$]-hept-3-yl)-alpha-(1-methylethenyl)-2-propanol; | | Low keyed woody note with trace of oily, woody, animal notes. |
| (ii) 29% 2-methyl-3-methylene alpha-(1-methylethenyl)-bicyclo-[2.2.1]-heptane-2-endo-propanol; and | | |
| (iii) 34% 2-methyl-3-methylene-alpha-(1-methylethenyl)-bicyclo-[2.2.1]-heptane-2-exo-propanol | | |

The novel processes of our invention involve:

A. A process for the preparation of at least one compound having a structure selected from the group consisting of:

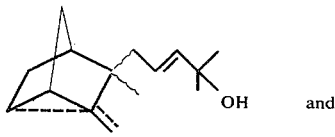 and

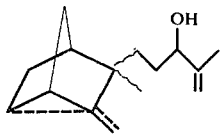

wherein one of the dashed lines is a carbon-carbon bond and each of the wavy lines is a carbon-carbon single bond, one of the carbon-carbon single bonds represented by the wavy line being epimeric with respect to the other of the carbon-carbon single bonds represented by the wavy line, comprising the steps of:

I. Subjecting one or more hydrocarbon compounds represented by the structure:

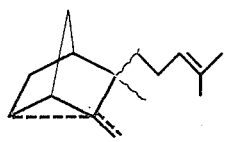

to an intense, oxidation step which comprises continuously insufflating air through said hydrocarbon compound, while agitating said hydrocarbon compound, and exposing said hydrocarbon compound to ultra violet light in the presence of a catalyst comprising an alkaline metal hydroxide and rose bengal; and II. Fractionally distilling the resulting reaction products.

B. A process for the preparation of at least one epoxide compound having the structure:

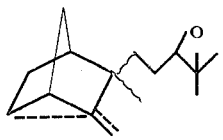

wherein one of the dashed lines is a carbon-carbon bond and each of the wavy lines is a carbon-carbon single bond, one of the carbon-carbon single bonds represented by the wavy line being epimeric with respect to the other of the carbon-carbon single bonds represented by the wavy line, comprising the steps of:

I. Reacting one or more hydrocarbon compounds represented by the structure:

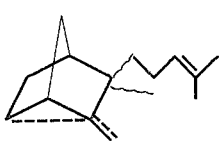

with a peracid selected from the group consisting of peracetic acid and perbenzoic acid at a temperature in the range of from −10° C up to +20° C and in the presence of an inert solvent and an alkali metal alkanoate and II. Fractionally distilling the reaction product.

C. A process for the preparation of at least one compound having the structure:

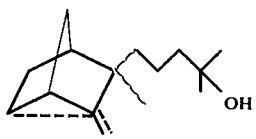

wherein one of the dashed lines is a carbon-carbon bond and each of the wavy lines is a carbon-carbon single bond, one of the carbon-carbon single bonds represented by the wavy lines being epimeric with respect to the other of the carbon-carbon single bonds represented by the wavy line, comprising the steps of:

I. Reacting one or more of the epoxide compounds produced according to Process B with lithium aluminum hydride in the presence of an inert solvent; and II. Fractionally distilling the resulting reaction products.

D. A process for the preparation of at least one tertiary alcohol compound having the structure:

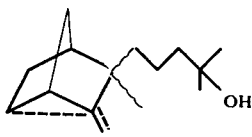

wherein one of the dashed lines is a carbon-carbon bond and each of the wavy lines is a carbon-carbon single bond, one of the carbon-carbon single bonds represented by the wavy line being epimeric with respect to the other of the carbon-carbon single bonds represented by the wavy line, comprising the steps of:

I. Reacting one or more of the epoxide compounds, produced according to Process B having the structure:

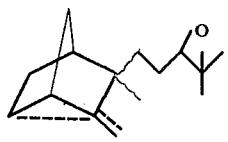

with lithium aluminum hydride and

III. Fractionally distilling the resulting reaction products.

E. A process for the preparation of at least one allylic tertiary alcohol compound having the structure:

wherein one of the dashed lines is a carbon-carbon bond and each of the wavy lines is a carbon-carbon single bond, one of the carbon-carbon single bonds represented by the wavy line being epimeric with respect to the other of the carbon-carbon single bonds represented by the wavy line, comprising the steps of:

I. Reacting one or more of the epoxide compounds, produced according to Process B having the structure:

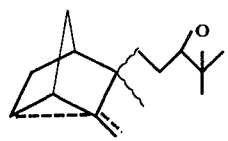

with diphenyl diselenide and sodium borohydride; and

II. Fractionally distilling the resulting reaction products.

F. A process for the preparation of at least one secondary allylic tertiary alcohol compound having the structure:

wherein one of the dashed lines is a carbon-carbon bond and each of the wavy lines is a carbon-carbon single bond, one of the carbon-carbon single bonds represented by the wavy line being epimeric with respect to the other of the carbon-carbon single bonds represented by the wavy line, comprising the steps of:

I. Reacting one or more of the epoxide compounds, produced according to Process B having the structure:

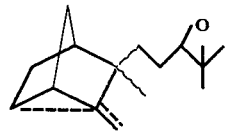

with aluminum isopropoxide, the ratio of aluminum isopropoxide: reactant being about 1:10;

II. Fractionally distilling the resulting reaction products.

Process "A" may be carried out using as a reactant a mixture of alpha-santalene, beta-santalene and epibeta-santalene or the individual compounds, produced either (i) synthetically per examples B, C and D infra or (ii) by means of distillation of saponified sandalwood oil according to example A infra.

The photooxidation step is preferably carried out in an inert solvent such as methanol or a methanolbenzene mixture in the presence of a reaction sensitizer such as rose bengal and a base such as sodium hydroxide and potassium hydroxide. The photooxidation is carried out by bubbling oxygen through the reaction mass and the time of reaction as well as the rate of reaction is a function of the following variables:

1. Bubble size of oxygen;
2. Throughput of oxygen per unit of time;
3. Pressure;
4. Concentration of base in reaction mass; and
5. Concentration of UV sensitizer in reaction mass.

Higher pressures give rise to longer oxygen residence time thereby permitting shorter times of reaction and greater yields per unit time. Higher concentrations of reaction sensitizer give rise to faster reaction rates:up to sensitizer concentrations of 5 per liter and sensitizer:santalene hydrocarbon ratios 0.5:4, whereat increase in sensitizer concentration does not give rise to any material increase in reaction rate. It is preferable to carry out photooxidation reaction at a temperature of between 15° C and 40° C with room temperature being most convenient.

The epoxidation reaction on one or more of the santalene hydrocarbons, alpha-santalene, beta-santalene and/or epi-beta-santalene is preferably carried out using a peracid such as peracetic acid, perhthalic acid or perbenzoic acid. The reaction is also carried out using an alkali metal lower alkanoate such as sodium acetate in an inert solvent, e.g., methylene chloride. The reaction temperature is preferably —10° C and +10° C with a range of 0°–5° C being preferred. The mole ratio of peracid to santalene hydrocarbon is preferably 1:1 with excess of any reactant giving rise to increased recovery problems. At the end of the reaction, the reaction mass is quenched with water destroying any undesired unreacted peracid. The concentration of santalene in solvent is preferably between 10 and 20% by weight.

The resultant epoxidized santalenes may be used as such in perfumery, or they may be reduced or rearranged to allylic tertiary alcohols or allylic secondary alcohols.

Reduction with strong reducing agents such as lithium aluminum hydride will give rise to one or more tertiary alcohols, as is illustrated in Example III, infra. The reduction of the epoxide using lithium aluminum hydride is preferably carried out in an inert volatile solvent such as diethyl ether at reflux (35° C and atmospheric pressure). It is preferable that the mole ratio of santalene epoxide: lithium aluminum hydride be about 1:1 since excess quantity of either reactant gives rise to high recovery costs and waste of reactant. At the end of the reaction the reaction mass is worked up by addition of an acid salt solution such as saturated ammonium chloride solution.

The rearrangement of the epoxide to the allylic tertiary alcohol is carried out using diphenyl diselenide and sodium borohydride, the mole ratio of diphenyl diselenide; sodium borohydride being preferred to be 1:2 and the mole ratio of sodium borohydride:diphenyl diselenide preferably being about 1:1. This reaction is preferably carried out in an inert anhydrous solvent at reflux temperature; preferably ethanol at 78° C. The reaction mass is preferably refluxed for a period of from one up to five hours in order to ensure complete reaction.

Where it is desired to rearrange the santalene epoxide to form allylic secondary alchohols, the reagent used is a catalytic quantity of aluminum isopropoxide. The reaction is carried out at a temperature in the range of 80° C up to 140° C over a period of between 2 and 6 hours. The preferable ratio of aluminum isopropoxide:santalene epoxide is 1:10 with a range of 1:20 up to 1:5 being workable.

When each of the foregoing reactions is complete, the particular reaction mixture is "worked-up" using routine purification procedures including the unit operations of extractions, crystallization, preparative chromatographic techniques, drying and/or distillation.

The polycycloalkyl oxyhydrocarbons of our invention having key sandalwood oil aroma notes can be used to contribute warm, sandal-like aromas.

Although not found, or found to be existent in relatively low proportions in sandalwood oil, the compounds of our invention are each considered to be at primary sandalwood aroma contributors of all of the constituents of sandalwood oil. Indeed, the relative strength of their aromas ae several-fold that of any other known aroma contributors heretofore found in sandalwood oil; and these properties are unexpected.

As olfactory agents the polycycloalkyl oxyhydrocarbons of this invention can be formulated into or used as components of a "perfume composition".

The term perfume composition is used herein to means a mixture of organic compounds, including, for example, alcohols, aldehydes, ketones, nitriles, esters, and frequently hydrocarbons which are admixed so that the combined odors of the individual components produce a pleasant or desired fragrance. Such perfume compositions usually contain: (a) the main note of the "bouquet" or foundation-stone of the composition; (b) modifiers which round-off and accompany the main note; (c) fixatives which include odorous substances which lend a particular note to the perfume throughout all stages of evaporation, and substances which retard evaporation; and (d) top-notes which are usually low-boiling fresh smelling materials.

In perfume compositions the individual component will contribute its particular olfactory characteristics, but the overall effect of the perfume composition will be the sum of the effect of each ingredient. Thus, the polycycloalkyl oxyhdyrocarbons of this invention, can be used to alter the aroma characteristics of a perfume composition, for example, by highlighting or moderating the olfactory reaction contributed by another ingredient in the composition.

The amount of the polycycloalkyl oxyhydrocarbons of this invention which will be effective in perfume compositions depends on many factors, including the other ingredients, their amounts and the effects which ae desired. It has been found that perfume compositions containing as little as 0.5 percent of the polycycloalkyl oxyhydrocarbons of this invention, or even less, can be used to impart a sandalwood scent to soaps, cosmetics, and the other products. The amount employed can range up to 50% or higher and will depend on considerations of cost, nature of the end product, the effect desired on the finished product and particular fragrance sought.

The polycycloalkyl oxyhydrocarbons of this invention can be used along or in a perfume composition as an olfactory component in detergents and soaps, space odorants and deodorants; perfumes; colognes; toilet waters; bath salts; hair preparations such as lacquers, brilliantines, pomades, and shampoos; cosmetic preparations such as creams, deodorants, hand lotions, and sun screens; powders such as talcs, dusting powders, face powders, and the like. When used as an olfactory component of a perfumed article, as little as 0.01 percent of the polycycloalkyl oxyhydrocarbons will suffice to impart a warm sandalwood aroma. Generally, no more than 0.5 percent is required.

In addition, the perfume composition can contain a vehicle or carrier for the polycycloalkyl oxyhydrocarbons alone or with other ingredients. The vehicle can be a liquid such as an alcohol such as ethanol, a glycol such as propylene glycol, or the like. The carrier can be an absorbent solid such as a gum or components for encapsulating the composition.

The following examples I-LXXII are given to illustrate embodiments of the invention as it is presently preferred to practice it. It will be understood that these examples are illustrative, and the invention is not to be considered as restricted thereto except as indicated in the appended claims. It is to be understood that unless otherwise stated all parts, proportions and percentages are by weight. Examples A-D are given herein to set forth methods for preparing raw materials useful as reactants in carrying out the procedures of Examples I-LXXII.

EXAMPLE A

PREPARATION OF MIXTURE OF ALPHA-SANTALENE, BETA-SANTALENE AND EPI-BETA-SANTALENE a. Saponification of Sandalwood Oil Into a 50 gallon reaction vessel equipped with agitator, reflux cooling heat exchange, internal steam heating coils and baffles is placed 95 pounds of methyl alcohol. With stirring, 5 pounds of sodium hydroxide flakes are added to the methanol. 100 pounds of sandalwood oil E.I. are then added to the reaction mass which is then heated to reflux (71° C) at atmospheric pressure. The reaction mass is then refluxed at 71° C for a period of 6 hours. The methanol solvent is then stripped off while the pot temperature rises from 71° C up to 100° C. The reaction mass is then cooled to 80° C, and 100 pounds of water are then added thereto. The reaction mass is then acidified to a pH of 5.5 with acetic acid after which it is washed with water thereby bringing the pH to 7.

b. Distillation of Saponified Sandalwood Oil 1,000 pounds of sandalwood oil saponified according to the procedure of part (a) supra is charged to a batch distillation apparatus of the same design as set forth in British Pat. No. 752,784 issued on July 11, 1956. The distillation column has a capacity of 200 gallons.

At 0 reflux and 360 mm Hg pressure, traces of water are removed from the saponified sandalwood oil.

At 3 mm Hg pressure, a head temperature of 80°-100° C, a pot temperature in the range of 155°-160° C, and a reflux ratio of 9:1, 100 pounds of distillate is collected at a distillation rate of 32 pounds/hour.

Two portions of the resulting distillate are then column chromatographed and fractionally distilled as follows:

Portion A-1

50 g of distillate are column chromatographed through 500 g of 5% deactivated $SiO_2$ with 2 liters of isopentane yielding 35 g of hydrocarbon. This 35 g of hydrocarbon material is then distilled at 0.2 mm Hg pressure using a microvigreux column having a 2 inch head yielding the following fractions:

| Fraction No. | Liquid Temperature | Vapor Temperature | Weight of Fraction |
|---|---|---|---|
| 1 | 83 – 90° C | 55 – 60° C | 0.3 g |
| 2 | 92 | 61 | 1.3 g |
| 3 | 105 | 75 | 22.0 g |
| 4 | 130 | 75 | 8.8 g |
| 5 | 145 | 60 | 0.7 g |

Fraction No. 1 is discarded, and fractions 3 and 4 are combined.

Portion A-2

100 g of distillate are column chromatographed through 1000 g of 5% deactivated $SiO_2$ with 2.5 liters of isopentane yielding 75 g of hydrocarbon. This 75 g hydrocarbon material is then distilled at 1.0–1.5 mm Hg pressure using a microvigreux column having a 2 inch head yielding the following fractions:

| Fraction No. | Liquid Temperature | Vapor Temperature | Pressure | Weight of Fraction |
|---|---|---|---|---|
| 1 | 107° C | 75 – 94° C | 1.5 mm | 0.8 g |
| 2 | 108 | 85 | 1.2 | 16.0 |
| 3 | 107 | 98 | 1.2 | 23.4 |
| 4 | 114 | 95 | 1.0 | 17.0 |
| 5 | 155 | 85 | 1.0 | 7.2 |
| 6 | 170 | 75 | 1.0 | 0.5 |

Fractions 1 and 6 are discarded. Fractions 2–5 are combined. GLC analysis (Conditions: 25 feet × ¼ inch 5% Carbowax 20M column) indicated: 28.7% alpha santalene; 23.5% epi-beta-santalene and 47.6% beta-santalene (% calculated by area normalization).

GLC mass spectral and IR analysis confirm that the resulting distilled mixture is as follows:

| NAME | WEIGHT % | STRUCTURE |
|---|---|---|
| alpha-santalene | 25 % | 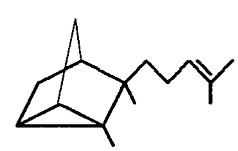 |
| epi-beta-santalene | 25 % | 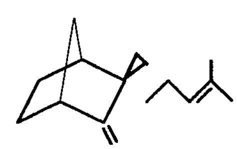 |
| Beta-santalene | 50 % | 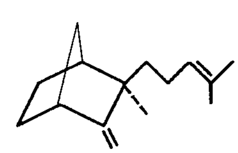 |

EXAMPLE B

SYNTHESIS OF ALPHA-SANTALENE 10 grams (0.046 moles) of π-bromotricyclene having the structure:

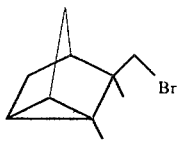

prepared according to the process of Corey et al., J. Am. Chem. Soc. 79, 5773 (1957) in 500 ml of absolute diethyl ether is added to 70 g (2.9 moles) of magnesium in 100 ml of ether during 7 hours. The mixture is heated at reflux for an additional 1.5 hours. The Grignard reagent is filtered through a glass-wood plug into γ,γ-dimethylallyl mesitoate (12.8 g., 0.055 mole, b.p. 95°–100° (0.1 mm.)) in 50 ml of ether. The time required for the addition was 2 hours. The excess magnesium is rinsed with 100 ml of ether and the washing is also added to the ester. The mixture is allowed to stand at room temperature for 96 hours. At the end of this time, a fine white percipitate appears in considerable quantity. To the ether solution is added with stirring a saturated ammonium chloride solution, and stirring is continued until both aqueous and ether layers are clear. The ether solution is washed with 10% sodium hydroxide, water and dried over sodium sulfate. The crude oil (12 g) after evaporation of ether is dissolved in pentane and chromatographed on alumina. The product is eluted with pentane and distilled to give two fractions: no. 1, 1.29 g., b.p. 56°–130° (15–20 mm.), $N^{25}D$ 1.4496; no. 2 2.81 g, b.p. 130°–140° (15–20 mm), $n^{25}D$ 1.4820. The residue from the distillation which solidified is largely bi-π-tricyclyl. Fraction 2 is redistilled, dissolved in pentane and chromatographed on alumina. The eluate is distilled and yields 1.7 g of oil, b.p. 116°–120° (8 ± 2 mm.), $n^{25}D$ 1.4822; infrared absorption at 1670, 858 and 840 cm$^{-1}$; alpha$^{26}D$ + 18.4°, +17.2° (pure liquid).

Anal. Calcd. for $C_{15}H_{24}$: C, 88.15; H, 11.84, Found: C, 88.06; H, 12.17.

The above constants for synthetic alpha-santalene agree well with those reported for the purest sample yet isolated from natural sources which had b.p. 116 (6 mm.), $n^{24}D$ 1.4855, alpha$^{24.8}D$ + 6.60°.

EXAMPLE C

PREPARATION OF BETA-SANTALENE

To 400 ml of a freshly prepared 1.2 molar methyl lithium solution in diethyl ether under a nitrogen blanket in a 3-necked flask, is added a solution of 2.54 g of endo-3-methyl-exo-3-(4-methyl-3-pentyl)-bicyclo-(2.2.1) heptanone-2-prepared according to the process of Corey et al., J.Am.Chem.Soc., 84 2611 (1962) in 15 ml of diethyl ether. The mixture is refluxed for 90 hours, decomposed by dropwise addition of water and worked up by separation of the ether layers and evaporation to give an oily product (2.76 g) whose infrared spectrum showed no carbonyl absorption but strong absorption at 2.8u due to hydroxyl. A portion of the crude hydroxy compound (1.535 g) is dissolved in a mixture of 20 ml of methylene chloride and treated at −5° with a solution of 5 ml of thionyl chloride in 5 ml of pyridine. After 10 minutes, 30 ml of pentane is added followed by 132 ml of 3 N hydrochloric acid. The pentane layer is separated, washed, dried and evaporated carefully after passage through a short column of alumina. Distillation of the residue affords 1.10 g of beta-santalene. The infrared and NMR spectra of this material are identical with that of beta-santalene of natural origin. The NMR spectrum (in carbon tetrachloride) shows a sharp peak due to tertiary methyl at 8.97, two peaks (not sharp) due to two methyl groups attached to double bond at 8.43 at 8.36 due to the two olefinic methylene protons ($J_{H-C-H}$ apparently almost 0) and a broader peak at ca. 5 due to the olefinic proton of the side chain. The characteristics peaks of epi-beta-santalene were completely lacking. Vapor phase chromatographic analysis of samples of the above product and purified natural beta-santalene on a 10 ft tricyanoethoxypropane (TCEP) column (25% on Chromasorb) at 135° shows that these behave identically (and that each was free of epi-beta-santalene). Pure natural beta-santalene is obtained by small scale preparative gas chromatography on the 10 ft TCEP column.

Anal. Calcd. for $C_{15}H_{24}$: C, 88.17; H, 11.83. Found: C, 88.15; H, 11.65.

EXAMPLE D

PREPARATION OF EPI-BETA-SANTALENE

The ketone, exo-3-methyl-endo-3-(4-methyl-3-pentenyl)-bicyclo-(2.2.1)-heptanone-2, prepared according to the process of Corey et al., J. Am. Chem. Soc., 84, 2611 (1962), dissolved in 10 ml of anhydrous ether is treated with 21.25 ml (0.034 mole) of 1.6 N methyllithium solution in ether at reflux under nitrogen for 5 days. This is cooled in an ice-bath, hydrolyzed with ice-water and worked up on the usual way to give 0.69 g (9.15%) of the desired hydroxy compound as a pale yellow liquid, showing infrared absorption at 2.71(w), 7.28(m) and 11.25(m) u. A portion of this product (0.223 g) dissolved in 5 ml of anhydrous pyridine and 1 ml of dry methylene chloride is cooled in an ice-salt bath below 0°, and treated with a cooled solution of 1 ml of pyridine and 1 ml of thionyl chloride. At the end of the addition, the brown mixture is kept at 0° for 10 minutes and then diluted with 10 ml of pentane followed by 27 ml of 3 N HCl (efficient cooling). The product is extracted with pentane, filtered through a column of alumina using pentane and distilled to give 0.14 g (69%) of epi-beta-santalene as a colorless liquid. The compound showed infrared absorption (in carbon tetrachloride) at 3.2(w), 6.02(m) and 11.3(s) u and on vapor phase chromatography on a 10 ft tricyanoethoxypropane column (25% on Chromasorb) at 135° with a helium flow rate of 33 ml./min. gives a retention time of 37 min. 20 sec. A mixture of the synthetic and the natural (isolated from natural beta-santalene sample) epi-beta-santalene gives a single peak with the same retention time under the above conditions while pure beta-santalene (both synthetic and natural) gave the retention time of 38 min. 55 sec. In the NMR spectrum (in carbon tetrahcloride) the exomethyl proton of the side chain shows up as a single peak at 8.38 and the three olefinic protons show up at 4.92 (side chain), 5.38 (terminal methylene) and 5.61 (terminal ethylene), respectively.

EXAMPLE I (A) PHOTOOXIDATION OF HYDROCARBONS OF SANDALWOOD OIL

Reaction:

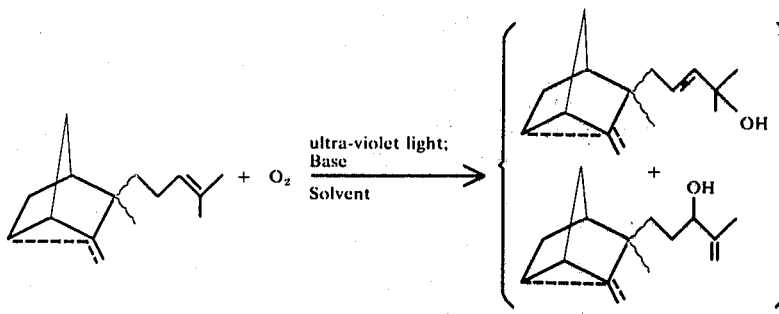

Procedure:

4 g of the hydrocarbons of sandalwood oil produced according to the process of Example A in 150 ml of benzene admixed with 0.5 g of rose bengal and stirred in the presence of ultraviolet light. Oxygen is then slowly bubbled into the reaction mass. The photooxidation is ceased after 100 hours. The solution is filtered and evaporated yielding approximately 4 g of the photooxidized product.

3 g of the reaction product is then separated using column chromatography on a column containing 75 g of 5% deactivated silicic acid as follows:

| Fraction | Solvent and Quantity of Solvent |
|---|---|
| 1 | 300 ml isopentane |
| 2 | 200 ml mixture of 2% diethyl ether in isopentane |
| 3 | 200 ml of mixture of 2% diethyl ether in isopentane |
| 4 | 200 ml mixture of 6% diethyl ether in isopentane |
| 5 | 200 ml mixture of 8% diethyl ether in isopentane |
| 6 | 200 ml mixture of 10% diethyl ether in isopentane |
| 7 | 200 ml mixture of 10% diethyl ether in isopentane |
| 8 | 200 ml mixture of 12% diethyl ether in isopentane |
| 9 | 200 ml mixture of 15% diethyl ether in isopentane |
| 10 | 200 ml mixture of 20% diethyl ether in isopentane |
| 11 | 200 ml mixture of 25% diethyl ether in isopentane |

Fraction 6 is then injected into gas-liquid chromatography apparatus on a 5% Carbowax column (25 feet × 1/8 inches) yielding 20 peaks. Peak 12 is identified by infrared, mass spectral and nuclear magnetic resonance analyses as 2-methyl-5-(2-methyl-3-methylene bicyclo (2.2.1) heptyl)-3-penten-2-ol, having the structure:

EXAMPLE I
(B) PHOTOOXIDATION OF HYDROCARBONS OF SANDALWOOD OIL

Reaction:

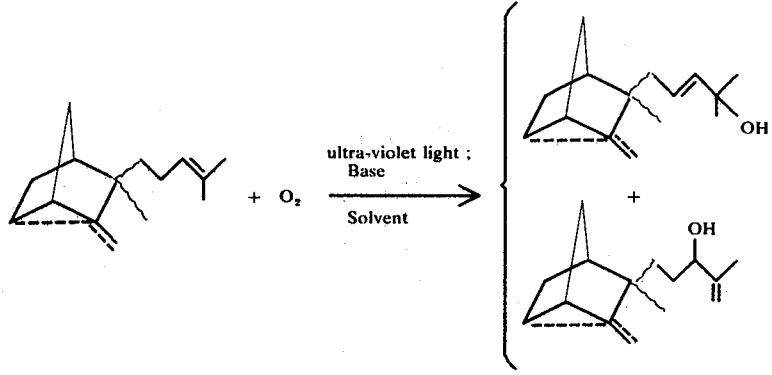

Procedure:

Into a one liter reaction flask equipped with magnetic stirrer, condenser, oxygen dispersion tube and thermometer, the following materials are added:

| | |
|---|---|
| Sandalwood oil hydrocarbons produced according to Example A Portion 1-A | 30.8 g |
| Absolute Methanol | 200 ml |
| Benzene | 200 ml |
| Sodium hydroxide | 0.5 g |
| Rose bengal | 0.2 g |

While monitoring the reaction using GLC apparatus (25 feet × ¼ inch 5% Carbowax 20M column) the reaction mass is photooxidized using an open pyrex system (450 watt Hanevia lamp) while bubbling oxygen into the reaction mass via the dispersion tube over a period of 14 hours. At the end of the 14 hour period, the hydrocarbon peaks are substantially completely eliminated.

The reaction mass is then concentrated at 60° C on an evaporator and 70 ml of water is added thereto. The reaction mass is then extracted with three 50 ml portions of diethyl ether and the ether extract is washed with several portions of saturated sodium chloride solution until the washings have a pH of 7. The ether extract is then dried over anhydrous magnesium sulfate and evaporated to obtain 27 g of crude product. The crude product is then distilled on a microvigreux column to yield the following fractions:

| Fraction No. | Liquid Temperature | Vapor Temperature | Weight of Fraction | Pressure (mm Hg) |
|---|---|---|---|---|
| 1 | 129° C | 72° C | 0.6 g | 0.5 |
| 2 | 122 | 97 | 1.3 | 0.5 |
| 3 | 140 | 65 | 0.6 | 0.5 |
| 4 | 122 | 72 | 2.2 | 0.5 |
| 5 | 133 | 106 | 2.8 | 0.4 |
| 6 | 154 | 109 | 4.9 | 0.4 |
| 7 | 175 | 125 | 1.2 | 0.4 |
| 8 | 200 | 126 | 2.0 | 0.4 |

Fractions 2–7 (weighing 9.9 g) are combined (Distillate Portion 1-B-1) after removing some material for future work.

Into a two liter reaction flask equipped with magnetic stirrer, condenser, oxygen dispersion tube and thermometer, the following materials are added:

| | |
|---|---|
| Sandalwood oil Hydrocarbons produced according to Example A, Portion 1-B | 60 g |
| Benzene | 350 ml |
| Absolute Methanol | 350 ml |
| Sodium Hydroxide | 1.0 g |
| Rose Bengal | 0.4 g |

While monitoring the reaction using GLC apparatus (25 feet × ¼ inch) 5% Carbowax 20M column) the reaction mass is photooxidized using an open pyrex system (450 watt Hanevia lamp), while bubbling oxygen into the reaction mass via the dispersion tube over a period of 21 hours. At the end of the 21 hour period, the hydrocarbon peaks are substantially eliminated.

The crude reaction product is then concentrated in an evaporator, and 100 ml water is added thereto. The reaction mass is then extracted with five 100 ml portions of diethyl ether and the ether extracts are combined. The combined ether extract is then washed with successive portions of saturated sodium chloride solution until the pH of the washings are at 7. The ether extract is then dried over anhydrous magnesium sulfate to obtain 67.0 g of a crude material. The crude product is then distilled on a microvigreux column to yield the following fractions:

| Fraction No. | Liquid Temperature | Vapor Temperature | Weight of Fraction | Pressure (mm Hg) |
|---|---|---|---|---|
| 1 | 130° C | 90 – 130° C | 4.0 g | 1.0 |
| 2 | 127 | 97 | 7.7 | 0.4 |
| 3 | 137 | 115 | 8.6 | 0.5 |
| 4 | 167 | 120 | 15.1 | 0.5 |
| 5 | 182 | 121 | 5.4 | 0.1 |

Fractions 2–5 (weighing 32.6 g) are combined (Distillate Portion 1-B-2). Distillate portions 1-B-1 and 1-B-2 are then combined yielding 42.5 g material. 42.0 g of this material is then column chromatographed over 500 g of 5% deactivated silica using isopentane or mixtures of diethyl ether and isopentane, as follows:

| Fraction No. | Solvent | Volume of Solvent | Weight of Distillate Recovered |
|---|---|---|---|
| 1 | 100% isopentane | 1000 ml | 9.2 g |
| 2 | 2% diethylether in isopentane | 500 | 0.6 |
| 3 | 4% diethylether in isopentane | 500 | 0.8 |
| 4 | 5% diethylether in isopentane | 150 | 1.5 |
| 5 | 5% diethylether in isopentane | 150 | 1.4 |
| 6 | 5% diethylether in isopentane | 150 | 0.7 |
| 7 | 5% diethylether in isopentane | 150 | 1.3 |
| 8 | 5% diethylether in isopentane | 150 | 1.2 |
| 9 | 5% diethylether in isopentane | 150 | 1.0 |
| 10 | 5% diethylether in isopentane | 150 | 0.9 |
| 11 | 5% diethylether in isopentane | 150 | 0.6 |
| 12 | 5% diethylether in isopentane | 150 | 0.6 |
| 13 | 5% diethylether in isopentane | 150 | 0.5 |
| 14 | 5% diethylether in isopentane | 150 | 0.5 |
| 15 | 5% diethylether in isopentane | 150 | 0.6 |
| 16 | 5% diethylether in isopentane | 150 | 0.6 |
| 17 | 5% diethylether in isopentane | 150 | 0.4 |
| 18 | 5% diethylether in isopentane | 150 | 0.5 |
| 19 | 5% diethylether in isopentane | 150 | 0.5 |
| 20 | 5% diethylether in isopentane | 150 | 0.5 |
| 21 | 5% diethylether in isopentane | 150 | 0.5 |
| 22 | 5% diethylether in isopentane | 150 | 0.5 |
| 23 | 5% diethylether in isopentane | 150 | 0.5 |
| 24 | 5% diethylether in isopentane | 150 | 0.5 |
| 25 | 5% diethylether in isopentane | 150 | 0.6 |
| 26 | 5% diethylether in isopentane | 150 | 0.4 |
| 27 | 5% diethylether in isopentane | 150 | 0.3 |
| 28 | 5% diethylether in isopentane | 150 | 0.2 |
| 29 | 5% diethylether in isopentane | 150 | 0.3 |
| 30 | 5% diethylether in isopentane | 150 | 0.2 |
| 31 | 5% diethylether in isopentane | 150 | 0.3 |
| 32 | 5% diethylether in isopentane | 150 | 0.3 |
| 33 | 6% diethylether in isopentane | 150 | 0.3 |
| 34 | 6% diethylether in isopentane | 150 | 0.2 |
| 35 | 6% diethylether in isopentane | 150 | 0.3 |
| 36 | 6% diethylether in isopentane | 150 | 0.5 |
| 37 | 8% diethylether in isopentane | 150 | 0.8 |
| 38 | 10% diethylether in isopentane | 150 | 1.2 |
| 39 | 15% diethylether in isopentane | 150 | 0.4 |
| 40 | 20% diethylether in isopentane | 150 | 0.4 |
| 41 | 50% diethylether in isopentane | 150 | 0.4 |

Fractions 15–21 are combined; fractions 22–31 are combined; and fractions 32–38 are combined. Fractions 32–38, combined, is fractionally distilled on a micro distillation column to yield the following fractions:

| Fraction No. | Liquid Temperature | Vapor Temperature | Weight of Fraction | Pressure (mm Hg) |
|---|---|---|---|---|
| 1 | 83 – 85° C | 85 – 86° C | 0.5 g | 0.1 |
| 2 | 89 | 89 | 1.2 | 0.1 |
| 3 | 130 | 100 | 1.0 | 0.1 |
| 4 | 182 | 148 | 0.3 | 0.1 |

Each of the groups of combined fractions as well as the distillation fractions of column chromatography fraction 32–38 are trapped and rechromatogrammed in GLC apparatus (Conditions: 25 feet × ¼ inch 5% SE-30 Column) and each peak is analyzed using infra-red, nuclear magnetic resonance and mass spectral analysis. The results are as follows:

---

Fractions 15–21 are combined; fractions 22–31 are combined and fractions 32–38 are combined.
Fractions 32–38, combined is fractionally distilled on a micro-distillation column to yield the following fractions.

| Fraction No. | Liquid Temperature | Vapor Temperature | Weight of Fraction | Pressure (mm Hg) |
|---|---|---|---|---|
| 1 | 83–85° C | 85–86° C | 0.5 g | 0.1 |
| 2 | 89 | 89 | 1.2 | 0.1 |
| 3 | 130 | 100 | 1.0 | 0.1 |
| 4 | 182 | 148 | 0.3 | 0.1 |

Each of the groups of combined fractions as well as the distillation fractions of column chromatography fraction 32–38 are trapped and rechromatogrammed in GLC apparatus (conditions: 25′ × ¼″ - 5% SE-30 column) and each peak is analyzed using infra-red, nuclear magnetic resonance and mass spectral analysis. The results are as follows:

| GLC Peak No. and Structure | Column Chromatography Fractions 15–21 | Column Chromatography Fractions 22–31 | Column Chromatography Fractions 32–38 | Distillates of Fractions 32–38 | | | |
|---|---|---|---|---|---|---|---|
| | | | | Fr. 1 | Fr. 2 | Fr. 3 | Fr. 4 |
| Peak No. 1 | 17.75% | 21.5% | 14.3% | 17.7% | 14.4% | 9.7% | 7.5% |
| Peak No. 2a | 11.6% | 17.9% | 28.7% | 30.0% | 27.4% | 24.0% | 19.5% |
| Peak No. 2b | 17.0% | 26.0% | 37.8% | 36.0% | 36.1% | 37.2% | 31.6% |
| Peak No. 3 | 15.2% | 4.4% | 1.3% | 1.4% | 2.0% | 1.3% | 1.3% |
| Peak No. 4 UNKNOWN | 2.8% | 2.2% | 6.6% | 4.9% | 6.8% | 9.0% | 8.7% |
| Peak No. 5 | 12.9% | 6.2% | trace | trace | 1.0% | 1.4% | 0.8% |

-continued

| Peak No. 6 | 17.5% | 14.2% | 2.3% | 1.2% | 2.0% | 5.3% | 5.9% |
|---|---|---|---|---|---|---|---|
| 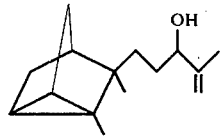 | | | | | | | |
| Peak No. 7 UNKNOWN | trace | 1.8% | 2.0% | trace | 1.6% | 6.6% | 9.9% |

ANALYTICAL DATA:
Structure:

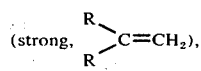

The infra-red analysis is as follows: 3.0 (-OH), 3.3, 3.4, 3.5, 6.0, 6.85, 7.25, 7.55, 7.7, 8.1, 8.3, 8.6, 8.9, 9.2, 9.45, 9.6, 9.8 (strong and broad), 10.2, 11.1

(strong, $\underset{R}{\overset{R}{>}}C=CH_2$), 11.7, 12.2.

The mass spectral analysis is as follows: m/e = 220 (M$^+$), 121, 93, 123, 91, 119.

The nuclear magnetic resonance spectral data is as follows:

| ppm | Interpretation | | Number of Protons |
|---|---|---|---|
| 0.82 | (s) | $CH_3-\underset{|}{\overset{|}{C}}-$ | 3H |
| 1.00 | (s) | $CH_3-\underset{|}{\overset{|}{C}}-$ | 3H |
| 1.74 | (s) | =C—CH$_3$ | 3H |
| 1.66–1.12 | (m) | $-CH_2-+H\underset{|}{\overset{|}{C}}-$ | 12H |
| 4.04 | (m) | $=C-\underset{H}{\overset{H}{C}}-O-$ | 1H |
| 4.90 | (d) | $\underset{H}{\overset{H}{>}}C=C\underset{|}{\overset{|}{<}}$ | 2H |

Structure:

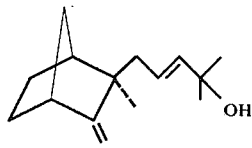

The infrared analysis is as follows: 3.0 (—OH), 3.29, 3.4, 3.5, 6.0, 6.7, 6.85, 6.95, 7.25, 7.5, 7.65, 8.1, 8.7 (broad), 9.0, 9.2, 9.65, 10.25 (strong, trans CH=CH), 10.75, 10.9, 11.35 (strong, >C=CH$_2$), 12.7, 13.4.

The mass spectral analysis is as follows: fragmentation (decreasing odor intensity except MOL ion) m/3 = 220 (M$^+$), 93, 121, 79, 41, 91.

The nuclear magnetic resonance spectral data is as follows:

| ppm | Interpretation | | Number of Protons |
|---|---|---|---|
| 1.10 | (s) | $CH_3-\underset{|}{\overset{|}{C}}-$ | 3H |
| 1.34 | (s) | $CH_3-\underset{\underset{CH_3}{|}}{\overset{|}{C}}-O-$ | 6H |
| 2.30–0.98 | (m) | $-CH_2-+H\underset{|}{\overset{|}{C}}-$ | 10H |
| 2.67 | (broad) | $=C-\overset{H}{C}-$ | 1H |
| 4.73 | (d) | $\underset{H}{\overset{H}{>}}C=C\underset{|}{\overset{|}{<}}$ | 2H |
| 5.73 | (m) | olefinic protons | 2H |

Structure:

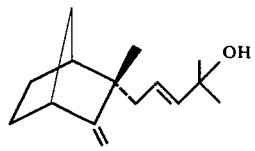

The infrared analysis is as follows: 3.0 (—OH), 3.2, 3.4, 3.5, 6.0, 6.8, 6.95, 7.25, 7.5, 7.65, 7.85, 8.1, 8.7 (broad), 9.0, 9.2, 9.6, 10.25 (Strong, trans CH=CH), 10.4, 10.75, 10.9, 11.35

(strong, $CH_2=C\underset{R}{\overset{R}{<}}$), 12.65, 12.9, 13.45.

The mass spectral analysis is as follows: major fragmentation pattern: (decreasing odor of intensity): m/e = 220 (M⁺), 93, 79, 121, 41, 91.

The nuclear magnetic resonance spectral data is as follows:

| ppm | | Interpretation | Number of Protons |
|---|---|---|---|
| 0.98 | (s) | CH₃—C— | 3H |
| 1.33 | (s) | CH₃—C—O— with CH₃ | 6H |
| 2.04–1.16 | (m) | —CH₂— and HC— | 10H |
| 2.68 | (broad) | =C—C—H | 1H |
| 4.62 | (d) | H,H>C=C— | 2H |
| 5.66 | (m) | olefinic protons | 2H |

Structure:

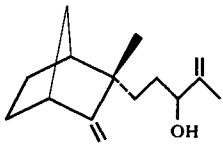

The infrared analysis is as follows: 3.0 (OH), 3.3, 3.4, 3.5, 6.0, 6.9, 7.25, 7.65, 7.8, 9.0, 9.45, 9.75, 9.95, 11.1 & 11.35 (Strong, C=CH₂)

The mass spectral analysis is as follows: m/e = 220 (M⁺), 93, 79, 121, 41, 81, 91.

The nuclear magnetic resonance spectral data is as follows:

| ppm | | Interpretation | Number of Protons |
|---|---|---|---|
| 1.00 | (s) | CH₃—C— | 3H |
| 1.76 | (s) | =C=CH₃ | 3H |
| 1.64–1.06 | (m) | —CH₂— | 11H |
| 2.00 | (broad) | (norbornyl H) | 1H |
| 2.70 | (broad) | (norbornyl H) | 1H |

| ppm | | Interpretation | Number of Protons |
|---|---|---|---|
| 4.04 | (broad) | HC—O— | 1H |
| 4.46 | (d) | 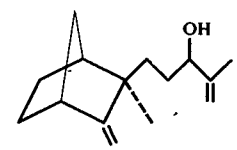 | 2H |
| 4.86 | (d) | H,H>C=C— | 2H |

Structure:

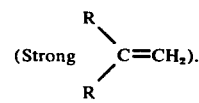

The infrared analysis is as follows: 3.0 (OH), 3.29, 3.4, 3.5, 6.0, 6.85, 7.05, 7.25, 7.65, 8.6, 8.85, 9.0, 9.2, 9.4, 9.7 (Strong, 11.1 & 11.35

(Strong R,R>C=CH₂).

The mass spectral analysis is as follows: m/e = 220 (M⁺), 93, 123, 79, 94, 121.

The nuclear magnetic resonance spectral data is as follows:

| ppm | | Interpretation | Number of Protons |
|---|---|---|---|
| 1.04 | (s) | CH₃—C— | (3H) |
| 1.74 | (s) | =C—CH₃ | (3H) |
| 1.68–1.12 | (m) | —CH₂— | (11H) |
| 2.06 | (broad) | (norbornyl H) | (1H) |
| 2.66 | (broad) | =C—C—H | (1H) |
| 4.00 | (m) | HC—O— | (1H) |

EXAMPLE I

(C) PHOTOOXIDATION OF ALPHA-SANTALENE

Reaction:

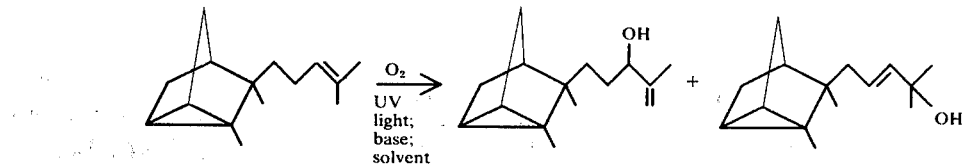

| ppm | Interpretation | Number of Protons |
|---|---|---|
| 4.62 | (d) | (2H) |
| 4.90 | (d) H\C=C−/H | (2H) |

Structure:

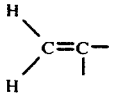

The infrared analysis is as follows: 3.0 (OH), 3.3, 3.4, 3.5, 6.85, 6.95, 7.25, 7.55, 7.75, 8.1, 8.25, 8.7 (Strong), 9.0, 9.25, 9.6, 9.8, 10.25 (Strong, trans CH=CH), 10.75, 10.99, 11.3, 11.7, 12.1, 12.35, 12.7.

The mass spectral analysis is as follows: m/e = 220 ($M^+$), 93, 121, 43, 41, 79, 91.

The nuclear magnetic resonance spectral data is as follows:

| ppm | Interpretation | | Number of Protons |
|---|---|---|---|
| 0.80 | (s) | $CH_3-\overset{\|}{\underset{\|}{C}}-$ | 3H |
| 1.02 | (s) | $CH_3-\overset{\|}{\underset{\|}{C}}-$ | 3H |
| 1.32 | (s) | $CH_3-\overset{\|}{\underset{CH_3}{C}}-O-$ | 6H |
| 1.90–1.08 | (m) | $-CH_2-+\overset{H}{C}$ | 10H |
| 5.60 | (m) | HC=CH | 2H |

Procedure:

Into a one liter reaction flask equipped with magnetic stirrer, condenser, oxygen dispersion tube and thermometer, the following materials are added:

| | |
|---|---|
| Alpha-santalene prepared according to Example B | 30.8 g |
| Absolute Methanol | 200 ml |
| Benzene | 200 ml |
| Sodium Hydroxide | 0.5 g |
| Rose Bengal | 0.2 g |

While monitoring the reaction using GLC apparatus (25 feet × ¼ inch 5% carbowax 20M column) the reaction mass is photooxidized using an open pyrex system (450 watt Manovia lamp) while bubbling oxygen into the reaction mass via the dispersion tube over a period of 16 hours. At the end of the 16-hour period, the hydrocarbon peak is substantially completely eliminated.

The reaction mass is then concentrated at 60° C in an evaporator, and 75 ml water is added thereto. The reaction mass is then extracted with three 50 ml portions of diethyl ether, and the ether extract is washed with several portions of sodium chloride solution until the washings have a pH of 7. The ether extract is then dried over anhydrous magnesium sulfate and evaporated to obtain 24 g of crude product. The crude product is then distilled on a microvigreux column and the resulting product is then analyzed using NMR, IR and mass spectral analysis confirming the presence of the following compounds:

5-(2,3-Dimethyl tricyclo (2.2.1.0$^{2,6}$)-hept-3-yl)-2-methyl-3-penten-2-ol 5-(2,3-Dimethyl tricyclo (2.2.1.0$^{2,6}$)-hept-3-yl)-2-methylene-pentan-3-ol

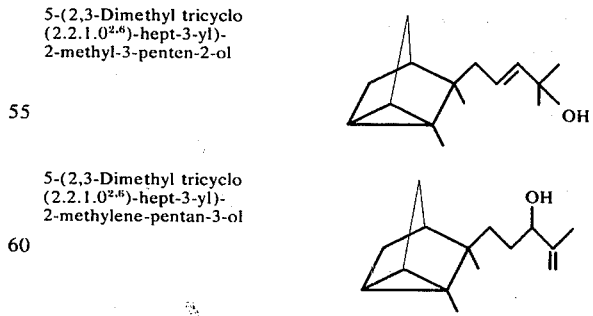

EXAMPLE I

(D) PHOTOOXIDATION OF BETA-SANTALENE

Reaction:

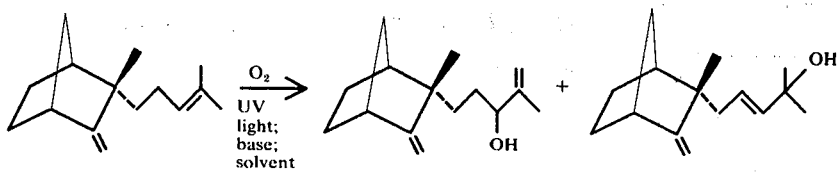

Procedure:

Into a one liter reaction flask equipped with magnetic stirrer, condenser, oxygen dispersion tube and thermometer, the following materials are added:

| | |
|---|---|
| Beta-santalene prepared according to Example C | 30.8 g |
| Absolute Methanol | 200 ml |
| Benzene | 200 ml |
| Sodium Hydroxide | 0.5 g |
| Rose Bengal | 0.2 g |

While monitoring the reaction using GLC apparatus (25 feet × ¼ inch 5% carbowax 20M column) the reaction mass is photooxidized using an open pyrex system (450 watt Manovia lamp) while bubbling oxygen into the reaction mass via the dispersion tube over a period of 16 hours. At the end of the 16-hour period, the hydrocarbon peak is substantially completely eliminated.

The reaction mass is then concentrated at 60° C in an evaporator, and 75 ml water is added thereto. The reaction mass is then extracted with three 50 ml portions of diethyl ether, and the ether extract is washed with several portions of sodium chloride solution until the washings have a pH of 7. The ether extract is then dried over anhydrous magnesium sulfate and evaporated to obtain 24 g of crude product. The crude product is then distilled on a micro vigreux column and the resulting product is then analyzed using NMR, IR and mass spectral analyses confirming the presence of the following compounds.

2-Methyl-5-(2-exo-methyl-3-methylene-bicyclo-(2.2.1)-hept-2-yl)-3-pentan-2-ol

2-Methyl-3-methylene alpha-(1-methylethenyl)-bicyclo(2.2.1)-heptane-2-endo-propanol

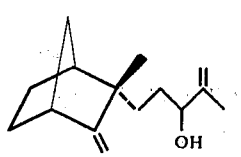

EXAMPLE I

(E) PHOTOOXIDATION OF EPI-BETA-SANTALENE

Reaction:

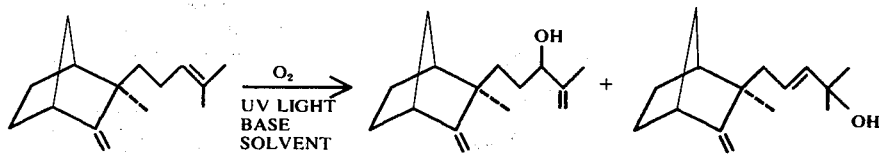

Procedure:

Into a one liter reaction flask equipped with magnetic stirrer, condenser, oxygen dispersion tube and thermometer, the following materials are added:

| | |
|---|---|
| Epi-beta-santalene produced according to Example D | 30.8 g |
| Absolute Methanol | 200 ml |
| Benzene | 200 ml |
| Sodium Hydroxide | 0.5 g |
| Rose Bengal | 0.2 g |

While monitoring the reaction using GLC apparatus (25 feet × ¼ inch 5% Carbowax column) the reaction mass is photooxidized using an open pyrex system (450 watt Manovia lamp) while bubbling oxygen into the reaction mass via the dispersion tube over a period of 16 hours. At the end of the 16-hour period, the hydrocarbon peak is substantially completely eliminated.

The reaction mass is then concentrated at 60° C in an evaporator, and 75 ml water is added thereto. The reaction mass is then extracted with three 50 ml portions of diethyl ether and the ether extract is washed with several portions of sodium chloride solution until the washings have a pH of 7. The ether extract is then dried over anhydrous magnesium sulfate and evaporated to obtain 25 g of crude product. The crude product is then distilled on a micro vigreux column and the resulting product is then analyzed using NMR, IR and mass spectral analysis confirming the presence of the following compound:

2-Methyl-5-(2-(endo)-methyl-3-methylene-bicyclo-(2.2.1)-hept-2-yl)-3-pentene-2-ol

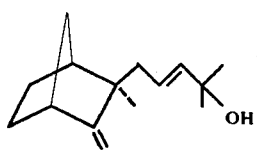

-continued

2-Methyl-3-methylene-alpha-
(1-methylene)-bicyclo-(2.2.1)-
heptane-2-exo-propanol

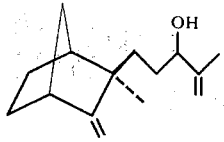

EXAMPLE II

(A) PREPARATION OF EPOXIDES OF SANTALENES

Reaction:

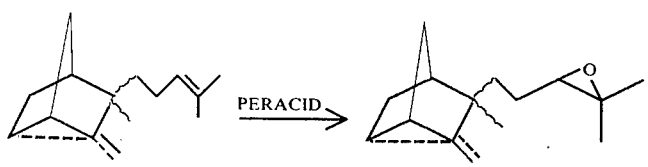

Procedure:

Into a one liter, 3-necked, round-bottom flask, equipped with stirrer, thermometer, condenser, dropping funnel and isopropyl alcohol-dry ice cooling bath, is placed 250 ml of methylene chloride and 56 g of sodium acetate. 36 g of the mixture of santalenes, alpha-santalene, beta-santalene and epi-beta-santalene, produced according to the process of Example A, is then added to the methylene chloride and sodium acetate. The reaction mass is cooled to 0°-5° C and 37.6 g of peracetic acid in 50 ml of methylene chloride is added, dropwise with stirring. Stirring continues for a period of 2½ hours while maintaining the temperature at 0°-5° C.

250 ml water is then added to the reaction mass. The aqueous phase is then separated from the organic phase, and the aqueous phase is washed with three 50 ml portions of methylene chloride. The methylene chloride washings are combined with the organic phase, and the combined methylene chloride solution is washed with five 50 ml portions of saturated sodium chloride solution. The organic phase is then dried over anhydrous magnesium sulfate and filtered. The solvent is evaporated yielding 31 g of epoxides which are distilled in three fractions as follows:

| Fraction No. | Vapor Temperature | Liquid Temperature | Pressure (mm Hg) | Weight of Fraction |
|---|---|---|---|---|
| 1 | 98° C | 116 – 118° C | 0.2 | 5.1 g |
| 2 | 100° C | 125° C | 0.2 | 15.8 g |
| 3 | 110° C | 140° C | 0.2 | 2.1 g |

GLC analysis, mass spectral analysis, nuclear magnetic resonance analysis, and infrared analysis confirm that the distilled material is made up of three compounds, to wit:

| Structure | Name | Per Cent |
|---|---|---|
| (A) | 5(2,3-Dimethyl tricyclo)(2.2.1.0$^{2,6}$)-hept-3-yl)-2-methyl-2,3-epoxypentane | 35% |
| (B) | 2-methyl-5(2-exomethyl-3-methylene-bicyclo-(2.2.1)-hept-2-yl)-2,3-epoxypentane | 13% |
| (C) | 2-methyl-5(2-endo-methyl-3-methylene-bicyclo-(2.2.1)-hept-2-yl)2,3-epoxypentane | 50% |

EXAMPLE II

(B) PREPARATION OF EPOXIDES OF α-SANTALENE

Reaction:

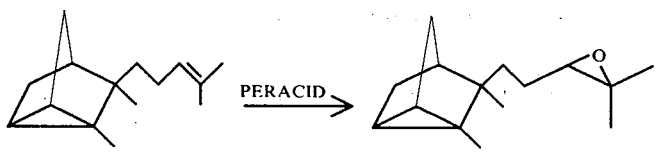

Procedure:

Into a one liter, 3-necked, round-bottom flask, equipped with stirrer, thermometer, condenser, dropping funnel and isopropyl alcohol-dry ice cooling bath, is placed 250 ml of methylene chloride and 56 g of sodium acetate. 36 g of the alpha-santalene produced according to the process of Example B, is then added to the methylene chloride and sodium acetate. The reaction mass is cooled to 0°–5° C and 37.6 g of peracetic acid in 50 ml of methylene chloride is added, dropwise, with stirring. Stirring continues for a period of 2½ hours while maintaining the temperature at 0°–5° C.

250 ml water is then added to the reaction mass. The aqueous phase is then separated from the organic phase, and the aqueous phase is washed with three 50 ml portions of methylene chloride. The methylene chloride washings are combined with the organic phase, and the combined methylene chloride solution is washed with five 50 ml portions of saturated sodium chloride solution. The organic phase is then dried over anhydrous magnesium sulfate and filtered. The solvent is evaporated yielding 30 g of epoxide having the structure:

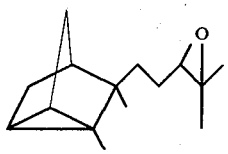

EXAMPLE II

(C) PREPARATION OF EPOXIDES OF BETA-SANTALENES

Reaction:

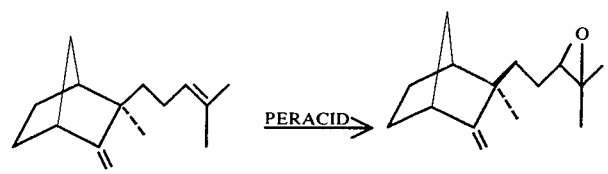

Procedure:

Into a one liter, 3-necked, round-bottom flask, equipped with stirrer, thermometer, condenser, dropping funnel and isopropyl alcohol-dry ice cooling bath, is placed 250 ml of methylene chloride and 56 g of sodium acetate. 36 g of the beta-santalene produced according to the process of Example C is then added to the methylene chloride and sodium acetate. The reaction mass is cooled to 0°–5° C and 37.6 g of peracetic acid in 50 ml of methylene chloride is added, dropwise, with stirring. Stirring continues for a period of 2½ hours while maintaining the temperature at 0°–5° C.

250 ml water is then added to the reaction mass. The aqueous phase is then separated from the organic phase, and the aqueous phase is washed with three 50 ml portions of methylene chloride. The methylene chloride washings are combined with the organic phase, and the combined methylene chloride solution is washed with five 50 ml portions of saturated sodium chloride solution. The organic phase is then dried over anhydrous magnesium sulfate and filtered. The solvent is evaporated yielding 29 g of beta-santalene epoxide having the structure:

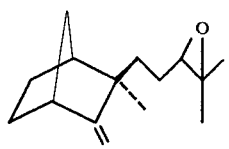

EXAMPLE II

(D) PREPARATION OF EPOXIDE OF EPI-BETA-SANTALENES

Reaction:

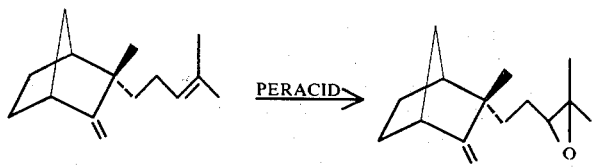

Procedure:

Into a one liter, 3-necked, round-bottom flask, equipped with stirrer, thermometer, condenser, dropping funnel and isopropyl alcohol-dry ice cooling bath, is placed 250 ml of methylene chloride and 56 g of sodium acetate. 36 g of the epi-beta-santalene, produced according to the process of Example D, is then added to the methylene chloride and sodium acetate. The reaction mass is cooled to 0°–5° C and 37.6 g of peracetic acid in 50 ml of methylene chloride is added, dropwise, with stirring. Stirring continues for a period of 2½ hours while maintaining the temperature at 0°–5° C.

250 ml water is then added to the reaction mass. The aqueous phase is then separated from the organic phase, and the aqueous phase is washed with three 50 ml portions of methylene chloride. The methylene chloride washings are combined with the organic phase, and the combined methylene chloride solution is washed with five 50 ml portions of saturated sodium chloride solution. The organic phase is then dried over anhydrous magnesium sulfate and filtered. The solvent is evaporated yielding 28 g of epi-beta-santalene epoxide having the structure:

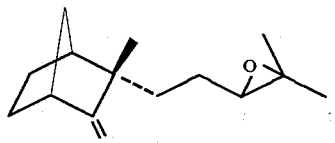

EXAMPLE III

(A) REDUCTION OF EPOXIDES OF SANTALENES TO FORM TERTIARY ALCOHOLS

Reaction:

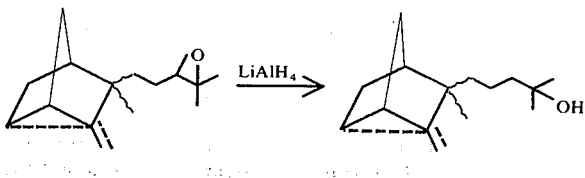

Procedure:

Into a 50 ml round-bottom reaction flask equipped with a condenser, thermometer, magnetic stirrer and heating mantle is placed 20 ml of diethyl ether. 0.5 g of the santalene epoxide reaction product produced according to Example II(A) is then added to the 20 ml of ether in the 50 ml flask. 0.3 g of lithium aluminum hydroxide is then slowly added, and the reaction mass is then refluxed for a period of three hours. After cooling, 15 ml of a saturated solution of $NH_4Cl$ is added to the reaction mass. The resulting mixture is filtered and the ether layer is separated from the aqueous phase. The aqueous phase is then extracted with two 20 ml portions of diethyl ether. The ether solutions are combined and washed with three 15 ml portions of saturated NaCl solution. The ether solution is then dried over anhydrous $MgSO_4$ and filtered. Evaporation of the solvent yields 0.5 g of crude product. Analysis of the three major peaks (resulting from GLC separation) for this crude product shows the formation of the following compounds:

| Name | Structure |
|---|---|
| 5-(2,3-Dimethyl tricyclo [2.2.1.0$^{2,6}$]-hept-3-yl)-2-methyl-pentan-2-ol | 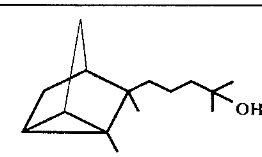 |
| 2-Methyl-5-(2-exo-methyl-3-methylene-bicyclo-[2.2.1]-hept-2-yl)-pentan-2-ol | 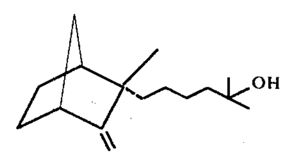 |
| 2-Methyl-5-(2-endo-methyl-3-methylene-bicyclo-[2.2.1]-hept-2-yl)-pentan-2-ol | 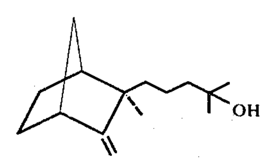 |

EXAMPLE III

(B) REDUCTION OF α-SANTALENE EPOXIDE TO FORM TERTIARY ALCOHOL

Reaction:

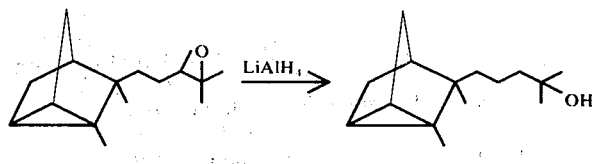

Procedure:

Into a 50 ml round-bottom reaction flask, equipped with a condenser, thermometer, magnetic stirrer and heating mantle is placed 20 ml of diethyl ether. 0.5 g of the santalene epoxide produced according to Example II(B) is then added to the 20 ml of ether in the 50 ml flask. 0.3 g of lithium aluminum hydride is slowly added, and the reaction mass is then refluxed for a period of three hours. After cooling, 15 ml of a saturated solution of NH$_4$Cl is added to the reaction mass. The resulting mixture is filtered and the ether layer is separated from the aqueous phase. The aqueous phase is then extracted with two 20 ml portions of diethyl ether. The ether solutions are combined and washed with three 15 ml portions of saturated NaCl solution. The ether solution is then dried over anhydrous MgSO$_4$ and filtered. Evaporation of the solvent yields 0.5 g of crude product. GLC analysis of the major peak for this crude product shows the formation of a compound having the structure:

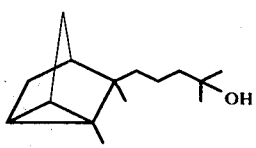

EXAMPLE III

(C) REDUCTION OF EPI-BETA SANTALENE EPOXIDE TO FORM TERTIARY ALCOHOL

Reaction:

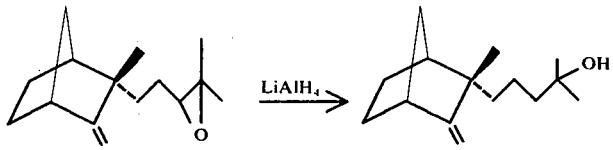

Procedure:

Into a 50 ml round-bottom reaction flask, equipped with a condenser, thermometer, magnetic stirrer and heating mantle is placed 20 ml of diethyl ether. 0.5 g of the beta-santalene epoxide produced according to Example II(C) is then added to the 20 ml of ether in the 50 ml flask. 0.3 g of lithium aluminum hydride is slowly added, and the reaction mass is then refluxed for a period of three hours. After cooling, 15 ml of a saturated solution of NH$_4$Cl is added to the reaction mass. The resulting mixture is filtered and the ether layer is separated from the aqueous phase. The aqueous phase is then extracted with two 20 ml portions of diethyl ether. The ether solutions are combined and washed with three 15 ml portions of saturated NaCl solution. The ether solution is then dried over anhydrous MgSO$_4$ and filtered. Evaporation of the solvent yields 0.5 g of crude product. GLC analysis of the major peak for this crude product shows the formation of a compound having the structure:

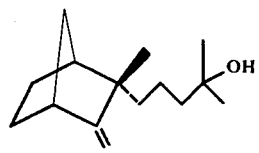

EXAMPLE III

(D) REDUCTION OF BETA-SANTALENE EPOXIDE TO FORM TERTIARY ALCOHOL

Reaction:

Procedure:

Into a 50 ml round-bottom reaction flask, equipped with a condenser, thermometer, magnetic stirrer and heating mantle is placed 20 ml of diethyl ether. 0.5 g of the santalene epoxide reaction product produced according to Example II(A) is then added to the 20 ml of ether in the 50 ml flask. 0.3 g of lithium aluminum hydride is then slowly added, and the reaction mass is then refluxed for a period of three hours. After cooling, 15 ml of a saturated solution of NH$_4$Cl is added to the reaction mass. The resulting mixture is filtered and the ether layer is separated from the aqueous phase. The aqueous phase is then extracted with two 20 ml portions of diethyl ether. The ether solutions are combined and washed with three 15 ml portions of saturated NaCl solution. The ether solution is then dried over anhydrous MgSO$_4$ and filtered. Evaporation of the solvent yields 0.5 g of crude product. Analysis of the major peak for this crude product shows the formation of the compound having the structure:

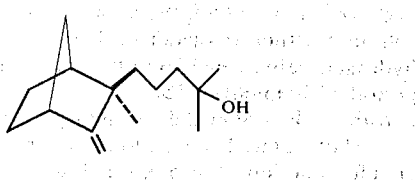

EXAMPLE IV

(A) REARRANGEMENT OF SANTALENE EPOXIDES TO ALLYLIC TERTIARY ALCOHOLS

Reaction:

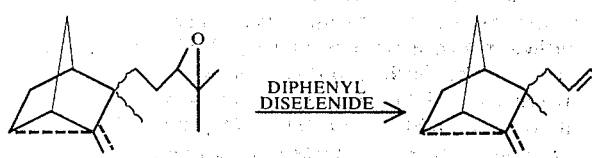

Procedure:

Into a one liter, three-necked round-bottom flask, equipped with stirrer, thermometer, nitrogen inlet tube and heating mantle is placed 200 ml of anhydrous ethanol. 12 g (0.04 moles) of diphenyl diselenide, (produced according to the procedure in J.Am.Chem.Soc., 95, 2697, Apr. 18, 1973) is then added to the ethanol. With stirring, 3.1 g (0.081 moles) of sodium borohydride is added under a nitrogen blanket. The color of the solution changes from bright yellow to colorless. 13.2 g of the mixture of alpha-beta-and epi-beta-santalene epoxides produced according to procedure of Example II(A) is then added and the reaction mass is refluxed at 78° C for a period of two hours. The solution is then cooled to room temperature and 100 ml of tetrahydrofuran is added thereto. The solution is then cooled to 10° C and 76 ml of 30% hydrogen peroxide (0.83 moles) is slowly added over a period of 30 minutes. The mixture is stirred for 2 hours and the contents of the reaction vessel is poured into 300 ml of water. The resulting mixture is then refrigerated for a period of 60 hours at 2° C. It is then extracted with five 150 ml portions of diethyl ether. The resulting ether solution is then washed with five 25 ml portions of saturated $Na_2CO_3$ solution followed by three 25 ml portions of saturated NaCl solution. The resulting ether solution is dried over anhydrous $MgSO_4$ and filtered. Evaporation of solvent yields 16 g of crude product (contaminated with selenium odor). The crude product is then placed in a 250 ml round bottom flask containing 100 ml of anhydrous ethanol. While stirring, 2 g of Raney nickel is then added. The resulting mixture is stirred for 2.5 hours at room temperature and then filtered through a celite filter. The ethanol is evaporated on a "rotovap" at elevated temperature, thus yielding 12 g of crude material.

The crude material is analyzed using GLC analysis on a 5% Carbowax 20M column (20 feet × ¼ inch). Formation of three compounds having the following structures is shown:

| Name | Structure |
|---|---|
| 5-(2,3-Dimethyl tricyclo (2.2.1.0$^{2,6}$)-hept-3-yl)-2-methyl-3-penten-2-ol | 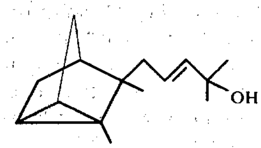 |
| 2-Methyl-5-(2-exo-methyl-3-methylene-bicyclo-(2.2.1)-hept-2-yl)-3-penten-2-ol | 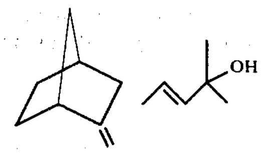 |
| 2-Methyl-5-(2-endo-methyl-3-methylene-bicyclo-(2.2.1)-hept-2-yl)-3-pentene-2-ol | 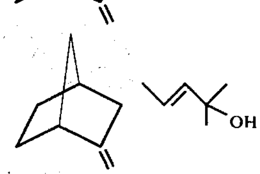 |

The GLC peaks are superimposable with those of the same compounds formed by means of the photooxidation of the mixture of alpha, beta and epi-beta santalenes in accordance with Example I(A).

EXAMPLE IV

(B) REARRANGEMENT OF α-SANTALENE EPOXIDE TO ALLYLIC TERTIARY ALCOHOL

Reaction:

Procedure:

Into a one liter, three-necked round-bottom flask equipped with stirrer, thermometer, nitrogen inlet tube and heating mantle is placed 200 ml of anhydrous ethanol. 12 g (0.04 moles) of diphenyl diselenide (produced according to the procedure in J.Am.Chem.Soc., 95, 2697, April 18, 1973) is then added to the ethanol. With stirring, 3.1 g (0.081 moles) of sodium borohydride is added under a nitrogen blanket. The color of the solution changes from bright yellow to colorless. 13.2 g of santalene epoxide produced according to procedure of Example II(B) is then added and the reaction mass is refluxed at 78° C for a period of two hours. The solution is then cooled to room temperature and 100 ml of tetrahydrofuran is added thereto. The solution is then cooled to 10° C and 76 ml of 30% hydrogen peroxide (0.83 moles) is slowly added over a period of 30 minutes. The mixture is stirred for 2 hours and the contents of the reaction vessel is poured into 300 ml of water. The resulting mixture is then refrigerated for a period of 60 hours at 2° C. It is then extracted with five 150 ml portions of diethyl ether. The resulting ether solution is then washed with five 25 ml portions of saturated $Na_2CO_3$ solution followed by three 25 ml portions of saturated NaCl solution. The resulting ether solution is dried over anhydrous $MgSO_4$ and filtered. Evaporation of solvent yields 16 g of crude product (contaminated with selenium odor). The crude product is then placed in a 250 ml round bottom flask containing 100 ml of anhydrous ethanol. While stirring, 2 g of Raney nickel is then added. The resulting mixture is stirred for 2.5 hours at room temperature and then filtered through a celite filter. The ethanol is evaporated on a rotovap evaporator at elevated temperature, thus yielding 12 g of crude material.

The crude material is analyzed using GLC analysis on a 5% Carbowax 20M column (20 feet × ¼ inch) and IR, NMR and mass spectral analysis. Formation is shown of a compound having the structure:

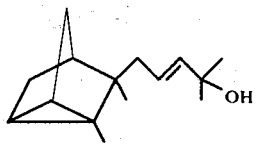

EXAMPLE IV

(C) REARRANGEMENT OF EPI-BETA-SANTALENE EPOXIDE TO ALLYLIC TERTIARY ALCOHOL

Reaction:

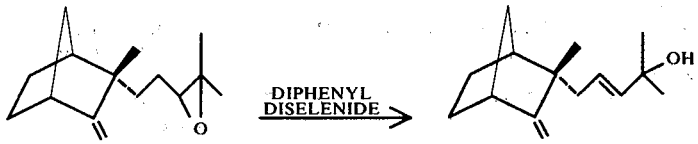

Procedure:

Into a one liter, three-necked round-bottom flask, equipped with stirrer, thermometer, nitrogen inlet tube and heating mantle is placed 200 ml of anhydrous ethanol. 12 g (0.04 moles) of diphenyl diselenide (produced according to the procedure in J.Am.Chem.Soc., 95, 2697, Apr. 18, 1973) is then added to the ethanol. With stirring, 3.1 g (0.081 moles) of sodium borohydride is added under a nitrogen blanket. The color of the solution changes from bright yellow to colorless. 13.2 g of beta-santalene epoxide produced according to procedure of Example II(C) is then added and the reaction mass is refluxed at 78° C for a period of two hours. The solution is then cooled to room temperature and 100 ml of tetrahydrofuran is added thereto. The solution is then cooled to 10° C and 76 ml of 30% hydrogen peroxide (0.83 moles) is slowly added over a period of 30 minutes. The mixture is stirred for 2 hours and the contents of the reaction vessel is poured into 300 ml of water. The resulting mixture is then refrigerated for a period of 60 hours at 2° C. It is then extracted with five 150 ml portions of diethyl ether. The resulting ether solution is then washed with five 25 ml portions of saturated $Na_2CO_3$ solution followed by three 25 ml portions of saturated NaCl solution. The resulting ether solution is dried over anhydrous $MgSO_4$ and filtered. Evaporation of solvent yields 16 g of crude product (contaminated with selenium odor). The crude product is then placed in a 250 ml round bottom flask containing 100 ml of anhydrous ethanol. While stirring, 2 g of Raney nickel is then added. The resulting mixture is stirred for 2.5 hours at room temperature and then filtered through a celite filter. The ethanol is evaporated on a rotovap evaporator at elevated temperature, thus yielding 12 g of crude material.

The crude material is analyzed using GLC analysis on a 5% Carbowax 20M column (20 feet × ¼ inch) and IR, NMR and mass spectral analyses. Formation is shown of a compound having the structure:

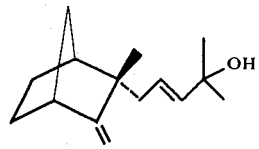

EXAMPLE IV

(D) REARRANGEMENT OF BETA-SANTALENE EPOXIDE TO ALLYLIC TERTIARY ALCOHOL

Reaction:

Procedure:

Into a one liter, three-necked round-bottom flask, equipped with stirrer, thermometer, nitrogen inlet tube and heating mantle is placed 200 ml of anhydrous ethanol. 12 g (0.04 moles) of diphenyl diselenide (produced according to the procedure in J.Am.Chem.Soc., 95, 2697, Apr. 18, 1973) is then added to the ethanol. With stirring, 3.1 g (0.081 moles) of sodium borohydride is added under a nitrogen blanket. The color of the solution changes from bright yellow to colorless. 13.2 g of the mixture of epi-beta-santalane epoxide produced according to procedures of Example II(D) is then added and the reaction mass is refluxed at 78° C for a period of two hours. The solution is then cooled to room temperature and 100 ml of tetrahydrofuran is added thereto. The solution is then cooled to 10° C and 76 ml of 30% hydrogen peroxide (0.83 moles) is slowly added over a period of 30 minutes. The mixture is stirred for 2 hours and the contents of the reaction vessel is poured into 300 ml of water. The resulting mixture is then refrigerated for a period of 60 hours, at 2° C. It is then extracted with five 150 ml portions of diethyl ether. The resulting ether solution is then washed with five 25 ml portions of saturated $Na_2CO_3$ solution followed by three 25 ml portions of saturated NaCl solution. The resulting ether solution is dried over anhydrous $MgSO_4$ and filtered. Evaporation of solvent yields 16 g of crude product (contaminated with selenium odor). The crude product is then placed in a 250 ml round bottom flask containing 100 ml of anhydrous ethanol. While stirring, 2 g of Raney nickel is then added. The resulting mixture is stirred for 2.5 hours at room temperature and then filtered through a celite filter. The ethanol is evaporated on a rotovap evaporator at elevated temperature, thus yielding 12 g of crude material.

The crude material is analyzed using GLC analyses on a 5% Carbowax 20M column (20 feet × ¼ inch) and IR, NMR and mass spectral analyses. Formation is shown of a compound having the structure:

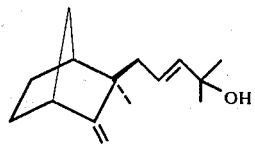

EXAMPLE V
(A) REARRANGEMENT OF SANTALENE EPOXIDES TO ALLYLIC SECONDARY ALCOHOLS

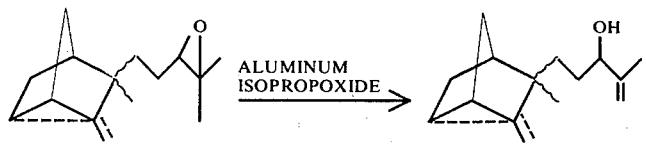

Procedure:

Into a 10 ml reaction flask equipped with stirrer, thermometer and a heating mantle is placed 2.2 grams (0.01 moles) of the mixture of alpha, beta and epi-beta santalene epoxides (Fraction 3) prepared according to the process of Example II(A).

0.24 g (0.001 moles) of aluminum isopropoxide is added. The reaction mass is then heated to 90° C and maintained at that temperature for a period of 4 hours. The reaction mass is then cooled to 25° C and the contents is poured into a beaker containing 20 g of ice. While stirring, 15 ml of 10% $H_2SO_4$ is added. The resulting aqueous phase is extracted with three 50 ml portions of diethyl ether. The resulting ether solution is then washed with three 25 ml portions of saturated NaCl solution, dried over anhydrous $MgSO_4$ and filtered. Evaporation of the solvent yields 2.2 g of crude product. GLC analysis on a 5% Carbowax 20M (20 feet × ¼ inch) column, IR, NMR and mass spectral analyses show that the following compounds are formed:

| Name | Structure |
|---|---|
| 2-Methyl-3-methylene alpha-(1-methylethenyl)-bicyclo-(2.2.1)-heptane-2-endo-propanol | 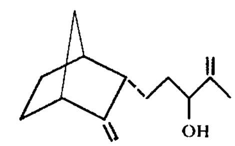 |
| 2-Methyl-3-methylene-alpha-(1-methylethenyl)-bicyclo-(2.2.1)-heptane-2-exo-propanol | 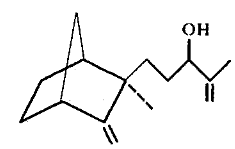 |
| 2,3-Dimethyl-alpha-(1-methylethenyl)-tricyclo-(2.2.1.0$^{2,6}$)-heptane-3-propanol | 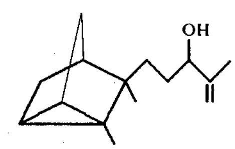 |

EXAMPLE V
(B) REARRANGEMENT OF α-SANTALENE EPOXIDE TO ALLYLIC SECONDARY ALCOHOL

Reaction:

Procedure:

Into a 10 ml reaction flask equipped with stirrer, thermometer and a heating mantle is placed 2.2 grams (0.01 moles) of alpha santalene epoxides prepared according to the process of Example II(B).

0.24 g (0.001 moles) of aluminum isopropoxide is added. The reaction mass is then heated to 90° C and maintained at that temperature for a period of 4 hours.

The reaction mass is then cooled to 25° C and the contents is poured into a beaker containing 20 g of ice. While stirring, 15 ml of 10% H₂SO₄ is added. The resulting aqueous phase is extracted with three 50 ml portions of diethyl ether. The resulting ether solution is then washed with three 25 ml portions of saturated NaCl solution, dried over anhydrous MgSO₄ and filtered. Evaporation of the solvent yields 2.2 g of crude product. GLC analysis on a 5% Carbowax 20M (20 feet × ¼ inch) column, IR, NMR and mass spectral analyses show that the compound having the following structure is formed:

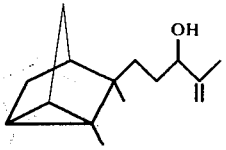

EXAMPLE V

(C) REARRANGEMENT OF EPI-BETA-SANTALENE EPOXIDE TO ALLYLIC SECONDARY ALCOHOL

Reaction:

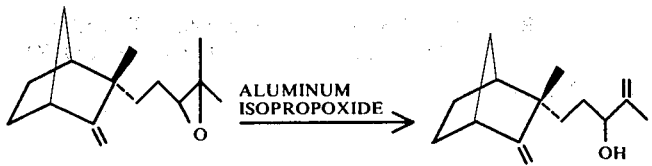

Procedure:

Into a 10 ml reaction flask equipped with stirrer, thermometer and a heating mantle is placed 2.2 grams (0.01 moles) of beta-santalene epoxide prepared according to the process of Example II(C).

0.24 g (0.001 moles) of aluminum isopropoxide is added. The reaction mass is then heated to 90° C and maintained at that temperature for a period of 4 hours. The reaction mass is then cooled to 25° C and the contents is poured into a beaker containing 20 g of ice. While stirring, 15 ml of 10% H₂SO₄ is added. The resulting aqueous phase is extracted with three 50 ml portions of diethyl ether. The resulting ether solution is then washed with three 25 ml portions of saturated NaCl solution, dried over anhydrous MgSO₄ and filtered. Evaporation of the solvent yields 2.2 g of crude product. GLC analysis on a 5% Carbowax 20M (20 feet × ¼ inch) column, IR, NMR and mass spectral analyses show that a compound having the following structure is formed.

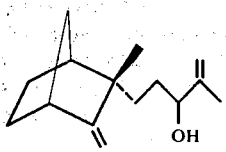

EXAMPLE V

(D) REARRANGEMENT OF BETA-SANTALENE EPOXIDE TO ALLYLIC SECONDARY ALCOHOL

Reaction:

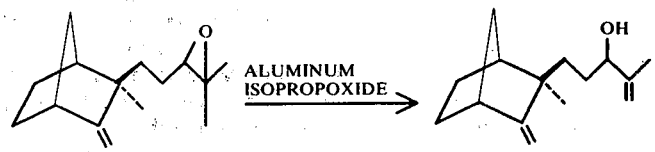

Procedure:

Into a 10 ml reaction flask equipped with stirrer, thermometer and a heating mantle is placed 2.2 grams (0.01 moles) of epi-beta-santalene epoxide prepared according to the present of Example II(D).

0.24 g (0.001 moles) of aluminum isopropoxide is added. The reaction mass is then heated to 90° C and maintained at that temperature for a period of 4 hours. The reaction mass is then cooled to 25° C and the contents is poured into a beaker containing 20 g of ice. While stirring, 15 ml of 10% H₂SO₄ is added. The resulting aqueous phase is extracted with three 50 ml portions of diethyl ether. The resulting ether solution is then washed with three 25 ml portions of saturated NaCl solution, dried over anhydrous MgSO₄ and filtered. Evaporation of the solvent yields 2.2 g of crude product. GLC analysis on a 5% Carbowax 20M (20 feet × ¼ inch) column, IR, NMR and mass spectral analyses show that a compound having the following structure is formed:

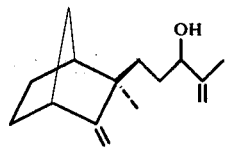

EXAMPLE VI

SANDAL COLOGNE FORMULATION

The following "Sandal Cologne" perfume formulation is prepared:

| Ingredients | Parts by Weight |
|---|---|
| Trimethyl-(2,2,3-norbornyl-5) 3-cyclohexanol-1 | 100 |
| 1',2',3',4',5',6',7',8'-octahydro-2',3',8',8'-tetramethyl-2'-aceto-naphthone isomer mixture produced according to the process of Example VII of Application for U.S. Letters Patent No. 434,948 filed on January 21, 1974 | 50 |
| 2,5,5-trimethyl acetyl cycloheptane produced according to Example I of U.S. Patent Application 349,180 filed on April 9, 1973 | 10 |
| Eugenol (10% sol. in diethyl phthalate) | 5 |
| Borneol (1% sol. in ethyl alcohol) | 2 |
| Cedrenal (A tricyclic sesquiterpinic aldehyde derived from cedrene, having the structure: | 15 |

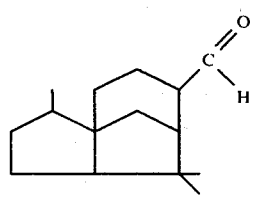

produced according to the process of U.S. Patent Application 260,537 filed on June 7, 1972 (corresponding to published Dutch Appl. 7307849 laid open for public inspection on December 11, 1973)

| | |
|---|---|
| 2,2-Dimethyl-3-(2-(2,3-dimethyl-tricyclo-(2,2,1,0$^{2,6}$)-hept-3-yl) ethyl)-oxirane having the structure: | 50 |

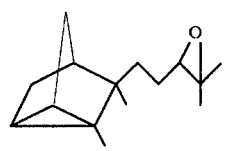

The 2,2-dimethyl-3-(2-(2,3-dimethyltricyclo(2,2,1,0$^{2,6}$)-hept-3-yl)ethyl)-oxirane imparts a green, woody note which is an important odor factor in East Indian Sandalwood.

EXAMPLE VII

SANDAL COLOGNE FORMULATION

The following sandal cologne perfume formulation is prepared:

| Ingredients | Parts by Weight |
|---|---|
| Bergamot Oil | 200 |
| Orange Flavor | 150 |
| Lemon Oil | 100 |
| Mandarin Oil | 50 |
| Eugenol | 10 |
| 4-(4-Methyl-4-hydroxy amyl) Δ³-cyclohexene carboxaldehyde | 50 |
| 3-methyl-4(2,6,6-trimethyl-2-cyclohexen-1-yl)3-buten-2-one | 30 |
| methyl-N-3,7-dimethyl-7-hydroxy-octylidene anthranilate | 5 |
| 6,7-dihydro-1,1,2,3,3-pentamethyl-4-(5H)-indanone having the structure: | 5 |
| prepared according to Prep. A of Swiss Patent 523,962 2-methyl-5-(2-endo-methyl-3-methylene-bicyclo-(2.2.1)-hept-2-yl)-3-penten-2-ol | 100 |

The 2-methyl-5-(2-endo-methyl-3-methylene-bicyclo(2.2.1)-hept-2-yl)-3-penten-2-ol imparts a warm, woody, sandal odor to the formulation.

EXAMPLE VIII

SANDAL COLOGNE FORMULATION

The following sandal cologne perfume formulation is prepared:

| Ingredients | Parts by Weight |
|---|---|
| Bergamot Oil | 200 |
| Orange Flavor | 150 |
| Lemon Oil | 100 |
| Mandarin Oil | 50 |
| Eugenol | 10 |
| 4-(4-Methyl-4-hydroxy amyl) Δ³-cyclohexene carboxaldehyde | 50 |
| 3-methyl-4(2,6,6-trimethyl-2-cyclohexen-1-yl)3-buten-2-one | 30 |
| methyl-N-3,7-dimethyl-7-hydroxy-octylidene anthranilate | 5 |
| 6,7-dihydro-1,1,2,3,3-pentamethyl-4 (5H) indanone having the structure: | 5 |
| prepared according to Prep. A of Swiss Patent 523,962 2-methyl-5(2-exo-methyl-3-methylene-bicyclo-(2.2.1)-hept-2-yl)3-penten-2-ol | 100 |

The 2-methyl-5(2-exo-methyl-3-methylene-bicyclo(2.2.1)-hept-2-yl)-3-penten-2-ol imparts a warm woody, sandal odor to the formulation.

EXAMPLE IX

SANDAL COLOGNE FORMULATION

The following sandal cologne perfume formulation is prepared:

| Ingredients | Parts by Weight |
|---|---|
| Bergamot Oil | 200 |
| Orange Flavor | 150 |
| Lemon Oil | 100 |
| Mandarin Oil | 50 |
| Eugenol | 10 |
| 4-(4-Methyl-4-hydroxy amyl) Δ³-cyclohexene carboxaldehyde | 50 |
| 3-methyl-4(2,6,6-trimethyl-2-cyclohexen-1-yl)3-buten-2-one | 30 |
| methyl-N-3,7-dimethyl-7-hydroxy-octylidene anthranilate | 5 |
| 6,7-dihydro-1,1,2,3,3-pentamethyl-4 (5H)-indanone having the structure: | 5 |

| Ingredients | Parts by Weight |
|---|---|

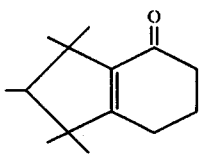

prepared according to Prep. A of
Swiss Patent 523,962
5(2,3-dimethyl tricyclo(2.2.1.0²,⁶)
hept-3-yl)2-methyl-3-penten-2-ol       100

The 5(2,3-dimethyl tricyclo(2.2.1.0²,⁶)hept-3-yl)2-methyl-3-penten-2-ol imparts a warm, woody, sandal odor to the formulation.

EXAMPLE X

SANDAL COLOGNE FORMULATION

The following sandal cologne perfume formulation is prepared:

| Ingredients | Parts by Weight |
|---|---|
| Bergamot Oil | 200 |
| Orange Flavor | 150 |
| Lemon Oil | 100 |
| Mandarin Oil | 50 |
| Eugenol | 10 |
| 4-(4-methyl-4-hydroxy amyl) Δ³-cyclohexene carboxaldehyde | 50 |
| 3-methyl-4(2,6,6-trimethyl-2-cyclohexen-1-yl)3-buten-2-one | 30 |
| methyl-N-3,7-dimethyl-7-hydroxy-octylidene anthranilate | 5 |
| 6,7-dihydro-1,1,2,3,3-pentamethyl-4 (5H) indanone having the structure: | 5 |

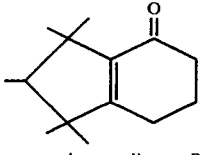

prepared according to Prep. A of
Swiss Patent 523,962
2,3-dimethyl alpha(1-methylethenyl)
tricyclo(2.2.1.0²,⁶) heptane-3-propanol       100

The 2,3-dimethyl alpha(1-methylethenyl) tricyclo (2.2.1.0²,⁶) heptane-3-propanol imparts a warm, woody, sandal odor to the formulation.

EXAMPLE XI

SANDAL COLOGNE FORMULATION

The following sandal cologne perfume formulation is prepared:

| Ingredients | Parts By Weight |
|---|---|
| Bergamot Oil | 200 |
| Orange Flavor | 150 |
| Lemon Oil | 100 |
| Mandarin Oil | 50 |
| Eugenol | 10 |
| 4-(4-methyl-4-hydroxy amyl) Δ³-cyclohexene carboxaldehyde | 50 |
| 3-methyl-4(2,6,6-trimethyl-2-cyclohexen-1-yl)3-buten-2-one | 30 |
| methyl-N-3,7-dimethyl-7-hydroxy-octylidene anthranilate | 5 |
| 6,7-dihydro-1,1,2,3,3-pentamethyl-4 (5H) indanone having the Structure: | 5 |

| Ingredients | Parts By Weight |
|---|---|

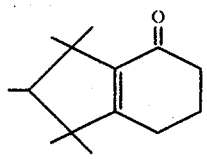

prepared according to Prep. A of
Swiss Patent 523,962
2-methyl-3-methylene-alpha(1-methyl-ethenyl) bicyclo(2.2.1) heptane-2-exo-propanol       100

The 2-methyl-3-methylene-alpha(1-methylethenyl) bicyclo-(2.2.1) heptane-2-exo-propanol imparts a warm, woody, sandal odor to the formulation.

EXAMPLE XII

SANDAL COLOGNE FORMULATION

The following sandal cologne perfume formulation is prepared:

| Ingredients | Parts by Weight |
|---|---|
| Bergamot Oil | 200 |
| Orange Flavor | 150 |
| Lemon Oil | 100 |
| Mandarin Oil | 50 |
| Eugenol | 10 |
| 4-(4-methyl-4-hydroxy amyl) Δ³-cyclohexene carboxaldehyde | 50 |
| 3-methyl-4(2,6,6-trimethyl-2-cyclohexen-1-yl)3-buten-2-one | 30 |
| methyl-N-3,7-dimethyl-7-hydroxy-octylidene anthranilate | 5 |
| 6,7-dihydro-1,1,2,3,3-pentamethyl-4 (5H) indanone having the structure: | 5 |

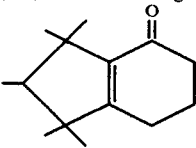

prepared according to Prep. A of
Swiss Patent 523,962
2-methyl-3-methylene alpha-(1-methyl-ethenyl) bicyclo(2.2.1)-heptane-2-endo-propanol       100

The 2-methyl-3-methylene alpha-(1-methylethenyl) bicyclo(2.2.1) heptane-2-endo-propanol imparts a warm, woody, sandal odor to the formulation.

EXAMPLE XIII

SANDAL COLOGNE FORMULATION

The following sandal cologne perfume formulation is prepared:

| Ingredients | Parts by Weight |
|---|---|
| Bergamot Oil | 200 |
| Orange Flavor | 150 |
| Lemon Oil | 100 |
| Mandarin Oil | 50 |
| Eugenol | 10 |
| 4-(4-methyl-4-hydroxy amyl) Δ³cyclohexene carboxaldehyde | 50 |
| 3-methyl-4(2,6,6-trimethyl-2-cyclohexen-1-yl)3-buten-2-one | 30 |
| methyl-N-3,7-dimethyl-7-hydroxy octylidene anthranilate | 5 |
| 6,7-dihydro-1,1,2,3,3-pentamethyl-4 (5H) indanone having the structure: | 5 |

| Ingredients | Parts by Weight |
|---|---|
| 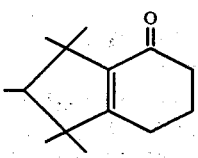 prepared according to Prep. A of Swiss Patent 523,962 | 100 |
| Mixture of: | |
| (i) 5-(2,3-dimethyl tricyclo (2.2.1.0$^{2,6}$)-hept-3-yl)-2-methyl-3-penten-2-ol | |
| (ii) 5-(2,3-dimethyl tricyclo (2.2.1.0$^{2,6}$)-hept-3-yl)-2-methyl-penten-2-ol | Produced according to Example I(A) |
| (iii) 2-methyl-5-(2-exo-methyl-3-methylene-bicyclo-(2.2.1) hept-2-yl)-penten-2-ol | |
| (iv) 2-methyl-5-(2-endo-methyl-3-methylene-bicyclo-(2.2.1)-hept-2-yl)-penten-2-ol | |
| (v) 2-methyl-5-(2-exo-methyl-3-methylene-bicyclo-(2.2.1)-hept-2-yl)-3-penten-2-ol | |
| The mixture of: | |
| (i) 5-(2,3-dimethyl tricyclo (2.2.1.0$^{2,6}$)-hept3-yl)-2-methyl-3-penten-2-ol | |
| (ii) 5-(2,3-dimethyl tricyclo 2.2.1.0$^{2,6}$)-hept-3-yl)-2-methyl-penten-2-ol | |
| (iii) 2-methyl-5-(2-exo-methyl-3-methylene-bicyclo-(2.2.1) hept-2-yl)-penten-2-ol | Produced according to Example I(A) |
| (iv) 2-methyl-4-(2-endo-methyl-3-methylene-bicyclo-(2.2.1) hept-2-yl)-penten-2-ol | |
| (v) 2-methyl-5-(2-exo-methyl-3-methylene-bicyclo-(2.2.1)-hept-2-yl)-3-penten-2-ol | | imparts a warm, woody, sandal odor to the formulation.

EXAMPLE XIV

PREPARATION OF A SOAP COMPOSITION

A total of 100 g of soap chips produced from unperfumed sodium base toilet soap made from tallow and coconut oil are mixed with 1 g of the perfume composition set forth in Example VII until a substantially homogeneous composition is obtained. The soap composition manifests a characteristic "sandal cologne" aroma having a warm, woody, sandal odor.

EXAMPLE XV

PREPARATION OF A SOAP COMPOSITION

A total of 100 g of soap chips produced from unperfumed sodium base toilet soap made from tallow and coconut oil is mixed with 1 g of 2-methyl-5-(2-endo-methyl-3-methylene bicyclo(2.2.1)-hept-2-yl)3-penten-2-ol until a substantially homogeneous composition is obtained. The soap composition manifests a sandalwood character with an oily, peanutlike, woody, green intense sandal aroma and with a wet bark top note.

EXAMPLE XVI

PREPARATION OF A DETERGENT COMPOSITION

A total of 100 g of a detergent powder sold under the trademark "RINSO" are mixed with 0.15 g of a perfume composition containing the mixture obtained in Example VII until a substantially homogeneous composition having a "sandal cologne" fragrance with a warm, woody, sandal odor is obtained.

EXAMPLE XVII

PREPARATION OF A COSMETIC BASE

A cosmetic powder is prepared by mixing 100 g of talcum powder with 0.25 g of the perfume composition of Example VII in a ball mill. A second cosmetic powder is similarly prepared except that the mixture produced in Example VII is replaced with the product produced in Example I(E), 2-methyl-5-(2-endo-methyl-3-methylene bicyclo(2.2.1)hept-2-yl)3-penten-2-ol. The cosmetic powder containing the material of Example VII has a "sandal cologne" fragrance with an oily, peanut-like, woody, green intense sandal aroma with a wet bark topnote character. The cosmetic powder produced using this material of Example I(E) has a sandalwood aroma with oily, peanut-like, woody, green intense sandal aroma with a wet bark topnote.

EXAMPLE XVIII

LIQUID DETERGENT CONTAINING 2-METHYL-5-(2-ENDO-METHYL-3-METHYLENE BICYCLO(2.2.1)HEPT-2-YL)3-PENTEN-2-OL

Concentrated liquid detergents with a sandalwood like odor containing 0.2%, 0.5% and 1.2% of the product produced in accordance with the process of Example I(E), 2-methyl-5-(2-endo-methyl-3-methylene bicyclo(2.2.1)hept-2-yl)3-penten-2-ol are prepared by adding the appropriate quantity of 2-methyl-5-(2-endo-methyl-3-methylene bicyclo(2.2.1)hept-2-yl)3-penten-2-ol to the liquid detergent known as P-87. The sandalwood aroma of the liquid detergent increases with increasing concentration of the 2-methyl-5-(2-endo-methyl-3-methylene bicyclo(2.2.1)hept-2-yl(3-penten-2-ol of this invention.

EXAMPLE XIX

PREPARATION OF COLOGNE AND HANDKERCHIEF PERFUME

The composition of Example VII is incorporated in a cologne having a concentration of 2.5% in 85% aqueous ethanol; and into a handkerchief perfume in a concentration of 20% (in 95% ethanol). The use of the composition of Example VII affords a distinct and definite "sandal cologne" aroma having a warm sandalwood-like character to the handkerchief perfume and to the cologne.

EXAMPLE XX

COLOGNE AND HANDKERCHIEF PERFUME

The 2-methyl-5-(2-endo-methyl-3-methylene bicyclo(2.2.1)hept-2-yl)-penten-2-ol produced by the process of Example IV(D) is incorporated into a cologne having a concentration of 2.5% in 85% ethanol; and into a handkerchief perfume in a concentration of 10% (in 95% ethanol). The 2-methyl-5-(2-endo-methyl-3-methylene bicyclo(2.2.1)hept-2-yl)3-penten-2-ol produced in Example IV(D) affords a distinct and definite sandalwood aroma with oily, peanut-like, woody, green intense sandal aroma with a wet bark topnote to the handkerchief perfume and to the cologne.

EXAMPLE XXI

PREPARATION OF A SOAP COMPOSITION

A total of 100 g of soap chips produced from unperfumed sodium base toilet soap made from tallow and coconut oil are mixed with 1 g of the perfume composition set forth in Example VIII until a substantially homogeneous composition is obtained. The soap composition manifests a characteristic "sandal cologne" aroma having a warm woody, sandal odor.

EXAMPLE XXII

PREPARATION OF A SOAP COMPOSITION

A total of 100 g of soap chips produced from unperfumed sodium base toilet soap made from tallow and coconut oil is mixed with 1 g of 2-methyl-5(2-exo-methyl-3-methylene bicyclo(2.2.1)hept-2-yl)3-penten-2-ol until a substantially homogeneous composition is obtained. The soap composition manifests a sandalwood character with oily, sandal, woody aroma with fruity nuances.

EXAMPLE XXIII

PREPARATION OF A DETERGENT COMPOSITION

A total of 100 g of a detergent powder sold under the trademark "RINSO" are mixed with 0.15 g of a perfume composition containing the mixture obtained in Example VIII until a substantially homogeneous composition having a "sandal cologne" fragrance with a warm woody, sandal odor is obtained.

EXAMPLE XXIV

PREPARATION OF A COSMETIC BASE

A cosmetic powder is prepared by mixing 100 g of talcum powder with 0.25 g of the perfume composition of Example VIII in a ball mill. A second cosmetic powder is similarly prepared except that the mixture produced in Example VIII is replaced with the product produced in Example IV(C), 2-methyl-5(2-exo-methyl-3-methylene bicyclo(2.2.1)hept-2-yl)3-penten-2-ol. The cosmetic powder containing the material of Example VIII has a "sandal cologne" fragrance with an warm woody, sandal aroma. The cosmetic powder produced using this material of Example IV(C) has an oily, sandal, woody aroma with fruity nuances.

EXAMPLE XXV

LIQUID DETERGENT CONTAINING 2-METHYL-5-(2-EXO-METHYL-3-METHYLENE BICYCLO(2.2.1)HEPT-2yl)3-PENTEN-2-OL

Concentrated liquid detergents with a sandalwood like odor containing 0.2%, 0.5% and 1.2% of the product produced in accordance with the process of Example VIII 2-methyl-5(2-exo-methyl-3-methylene bicyclo(2.2.1)hept-2-yl)3-penten-2-ol are prepared by adding the appropriate quantity of 2-methyl-5(2-exo-methyl-3-methylene bicyclo(2.2.1)hept-2yl)3-penten-2-ol to the liquid detergent known as P-87. The sandalwood aroma of the liquid detergent increases with increasing concentration of the 2-methyl-5(2-exo-methyl-3-methylene bicyclo(2.2.1)hept-2-yl)3-penten-2-ol of this invention.

EXAMPLE XXVI

PREPARATION OF COLOGNE AND HANDKERCHIEF PERFUME

The composition of Example VIII is incorporated in a cologne having a concentration of 2.5% in 85% aqueous ethanol; and into a handkerchief perfume in a concentration of 20% (in 95% ethanol). The use of the composition of Example VIII affords a distinct and definite "sandal cologne" aroma having a warm sandalwood-like character to the handkerchief perfume and to the cologne.

EXAMPLE XXVII

COLOGNE AND HANDKERCHIEF PERFUME

The 2-methyl-5(2-exo-methyl-3-methylene bicyclo(2.2.1)hept-2-yl)3-penten-2-ol produced by the process of Example IV(C) is incorporated into a cologne having a concentration of 2.5% in 85% ethanol; and into a handkerchief perfume in a concentration of 10% (in 95% ethanol). The 2-methyl-5(2-exo-methyl-3-methylene bicyclo(2.2.1)hept-2-yl)3-penten-2-ol produced in Example IV(C) affords a distinct and definite sandalwood aroma with oily, sandal, woody aroma with fruity nuances to the handkerchief perfume and to the cologne.

EXAMPLE XXVIII

PREPARATION OF A SOAP COMPOSITION

A total of 100 g of soap chips produced from unperfumed sodium base toilet soap made from tallow and coconut oil are mixed with 1 g of the perfume composition set forth in Example IX, until a substantially homogeneous composition is obtained. The soap composition manifests a characteristic "sandal cologne" aroma having a warm, woody, sandal odor.

EXAMPLE XXIX

PREPARATION OF A SOAP COMPOSITION

A total of 100 g of soap chips produced from unperfumed sodium base toilet soap made from tallow and coconut oil is mixed with 1 g of 5(2,3-dimethyl tricyclo(2.2.1.0$^{2,6}$)hept-3-yl)2-methyl-3-penten-2-ol until a substantially homogeneous composition is obtained. The soap composition manifests a sandalwood character with oily, woody, sweet, pumpkin, strong sandal, fruity, bready, slightly green, nutty aroma with floral, woody, slightly fatty, rosey and vetiverol-like notes.

EXAMPLE XXX

PREPARATION OF A DETERGENT COMPOSITION

A total of 100 g of a detergent powder sold under the trademark "RINSO" are mixed with 0.15 g of a perfume composition containing the mixture obtained in Example IX until a substantially homogeneous composition having a "sandal cologne" fragrance with a warm, woody, sandal odor is obtained.

EXAMPLE XXXI

PREPARATION OF A COSMETIC BASE

A cosmetic powder is prepared by mixing 100 g of talcum powder with 0.25 g of the perfume composition of Example IX in a ball mill. A second cosmetic powder is similarly prepared except that the mixture produced in Example IX is replaced with the product produced in Example IV(B), 5(2,3-dimethyl tricyclo(2.2.1.0$^{2,6}$)hept-3-yl)2-methyl-3-penten-2-ol. The cosmetic powder containing the material of Example IX has a "sandal cologne" fragrance with a woody, sandal character. The cosmetic powder produced using this material of Example IV(B) has a sandalwood aroma with oily, woody, sweet, pumpkin strong, sandal, fruity, bready, slightly green, nutty aroma with floral, woody, slightly fatty, rosey and vetiverol-like notes.

EXAMPLE XXXII

LIQUID DETERGENT CONTAINING 5(2,3-DIMETHYL TRICYCLO(2.2.1.$^{2,6}$)HEPT-3-YL)2-METHYL-3-PENTEN-2-OL

Concentrated liquid detergents with a sandalwood like odor containing 0.2%, 0.5% and 1.2% of the product produced in accordance with the process of Example IV(B), 5(2,3-dimethyl-tricyclo(2.2.1.0$^{2,6}$)hept-3-yl)2-methyl-3-penten-2-ol are prepared by adding the appropriate quantity of 5(2,3-dimethyl tricyclo(2.2.1.0$^{2,6}$)hept-3-yl)2-methyl-3-penten-2-ol to the liquid detergent known as P-87. The sandalwood aroma of the liquid detergent increases with increasing concentration of the 5(2,3-dimethyl tricyclo(2.2.1.0$^{2,6}$)hept-3-yl)2-methyl-3-penten-2-ol of this invention.

EXAMPLE XXXIII

PREPARATION OF COLOGNE AND HANDKERCHIEF PERFUME

The composition of Example IX is incorporated in a cologne having a concentration of 2.5% in 85% aqueous ethanol; and into a handkerchief perfume in a concentration of 20% (in 95% ethanol). The use of the composition of Example IX affords a distinct and definite "sandal cologne" aroma having a warm sandalwood-like character to the handkerchief perfume and to the cologne.

EXAMPLE XXXIV

COLOGNE AND HANDKERCHIEF PERFUME

The 5(2,3-dimethyl tricyclo(2.2.1.0$^{2,6}$)hept-3-yl)2-methyl-3-penten-2-ol produced by the process of Example IV(B) is incorporated into a cologne having a concentration of 2.5% in 85% ethanol; and into a handkerchief perfume in a concentration of 10% (in 95% ethanol). The 5(2,3-dimethyl tricyclo (2.2.1.0$^{2,6}$)hept-3-yl)2-methyl-3-penten-2-ol produced in Example IV(B) affords a distinct and definite sandalwood aroma with oily, woody, sweet, pumpkin, strong sandal, fruity, bready, slightly green, nutty aroma with floral, woody, slightly fatty, rosey and vetiverol-like notes, to the handkerchief perfume and to the cologne.

EXAMPLE XXXIV

PREPARATION OF A SOAP COMPOSITION

A total of 100 g of soap chips produced from unperfumed sodium base toilet soap made from tallow and coconut oil are mixed with 1 g of the perfume composition set forth in Example X until a substantially homogeneous composition is obtained. The soap composition manifests a characteristic "sandal cologne" aroma having a warm, woody, sandal odor.

EXAMPLE XXXV

PREPARATION OF A SOAP COMPOSITION

A total of 100 g of soap chips produced from unperfumed sodium base toilet soap made from tallow and coconut oil is mixed with 1 g of 2,3-dimethyl alpha(1-methylethenyl) tricyclo(2.2.1.0$^{2,6}$)heptane 3-propanol until a substantially homogeneous composition is obtained. The soap composition manifests a sandalwood character with a green, oily, woody, pine needlelike note.

EXAMPLE XXXVI

PREPARATION OF A DETERGENT COMPOSITION

A total of 100 g of a detergent powder sold under the trademark "RINSO" are mixed with 0.15 g of a perfume composition containing the mixture obtained in Example X until a substantially homogeneous composition having a "sandal cologne" fragrance with a warm, woody, sandal odor is obtained.

EXAMPLE XXXVII

PREPARATION OF A COSMETIC BASE

A cosmetic powder is prepared by mixing 100 g of talcum powder with 0.25 g of the perfume composition of Example X in a ball mill. A second cosmetic powder is similarly prepared except that the mixture produced in Example X is replaced with the product produced in Example V(B), 2,3-dimethyl alpha(1-methylethenyl) tricyclo(2.2.1.0$^{2,6}$)heptane-3-propanol.

The cosmetic powder containing the material of Example X has a "sandal cologne" fragrance with a warm, woody, sandal odor character. The cosmetic powder produced using this material of Example V(B) has a sandalwood aroma with a green, oily, woody, pine needle-like note.

EXAMPLE XXXVIII

LIQUID DETERGENT CONTAINING 2,3-DIMETHYL ALPHA(1-METHYLETHENYL)TRICYCLO(2.2.1.0$^{2,6}$)HEPTANE-3-PROPANOL

Concentrated liquid detergents with a patchoulilike odor containing 0.2%, 0.5% and 1.2% of the product produced in accordance with the process of Example X, 2,3-dimethyl alpha(1-methylethenyl) tricyclo(2.2.1.0$^{2,6}$) heptane-3-propanol are prepared by adding the appropriate quantity of 2,3-dimethyl alpha(1-methylethenyl) tricyclo(2.2.1.0$^{2,6}$)heptane-3-propanol to the liquid detergent known as P-87. The sandalwood aroma of the liquid detergent increases with increasing concentration of the 2,3-dimethyl alpha(1-methylethenyl) tricyclo(2.2.1.0$^{2,6}$)heptane-3-propanol of this invention.

EXAMPLE XXXIX

PREPARATION OF COLOGNE AND HANDKERCHIEF PERFUME

The composition of Example X is incorporated in a cologne having a concentration of 2.5% in 85% aqueous ethanol; and into a handkerchief perfume in a concentration of 20% (in 95% ethanol). The use of the composition of Example X affords a distinct and definite sandal cologne aroma having a warm sandalwood-like character to the handkerchief perfume and to the cologne.

EXAMPLE XL

COLOGNE AND HANDKERCHIEF PERFUME

The 2,3-dimethyl alpha(1-methylethenyl) tricyclo(2.2.1.0$^{2,6}$)heptane-3-propanol produced by the process of Example V(B) is incorporated into a cologne having a concentration of 2.5% in 85% ethanol; and into a handkerchief perfume in a concentration of 10% (in 95% ethanol). The 2,3-dimethyl alpha(1-methylethenyl) tricyclo(2.2.1.0$^{2,6}$)heptane-3-propanol produced in Example V(B) affords a distinct and definite sandalwood aroma with warm woody, sandal odor and green, oily, woody, pine-needle-like notes to the handkerchief perfume and to the cologne.

EXAMPLE XLI

PREPARATION OF A SOAP COMPOSITION

A total of 100 g of soap chips produced from unperfumed sodium base toilet soap made from tallow and coconut oil are mixed with 1 g of the perfume composition set forth in Example XI until a substantially homogeneous composition is obtained. The soap composition manifests a characteristic "sandal cologne" aroma having a warm, woody, sandal odor.

EXAMPLE XLII

PREPARATION OF A SOAP COMPOSITION

A total of 100 g of soap chips produced from unperfumed sodium base tiolet soap made from tallow and coconut oil is mixed with 1 g of 2-methyl-3-methylene-alpha(1-methylethenyl) bicyclo(2.2.1)heptane-2-exo-propanol until a substantially homogeneous composition is obtained. The soap composition manifests a sandalwood character with sweet, woody, fruity, oily, green aroma.

EXAMPLE XLIII

PREPARATION OF A DETERGENT COMPOSITION

A total of 100 g of a detergent powder sold under the trademark "RINSO" are mixed with 0.15 g of a perfume composition containing the mixture obtained in Example XI until a substantially homogeneous composition having a "sandal cologne" fragrance with a warm, woody, sandal odor is obtained.

EXAMPLE XLIV

PREPARATION OF A COSMETIC BASE

A cosmetic powder is prepared by mixing 100 g of talcum powder with b 0.25 g of the perfume composition of Example XI in a ball mill. A second cosmetic powder is similarly prepared except that the mixture produced in Example XI is replaced with the product produced in Example V(C), 2-methyl 3-methylene-alpha (1-methylethenyl) bicyclo(2,2,1)heptane-2-exo-propanol.

The cosmetic powder containing the material of Example XI has a "sandal cologne" fragrance with a warm, woody, sandal odor character. The cosmetic powder produced using this material of Example V(C) has a sandalwood aroma with a sweet, woody, fruity, oily, green aroma.

EXAMPLE XLV

LIQUID DETERGENT CONTAINING 2-METHYL-3-METHYLENE-ALPHA (1-METHYLETHENYL) BICYCLO(2.2.1)HEPTANE-2-EXO-PROPANOL

Concentrated liquid detergents with a patchoulilike odor containing 0.2%, 0.5% and 1.2% of the product produced in accordance with the process of Example V(C), 2-methyl-3-methylene-alpha(1-methylethenyl) bicyclo(2.2.1)heptane-2-exo-propanol are prepared by adding the appropriate quantity of 2-methyl-3-methylene-alpha(1-methylethenyl) bicyclo(2.2.1) heptane-2-exo-propanol to the liquid detergent known as P-87. The sandalwood aroma of the liquid detergent increases with increasing concentration of the 2-methyl-3-methylene-alpha(1-methylethenyl) bicyclo(2.2.1.)heptane-2-exo-propanol of this invention.

EXAMPLE XLVI

PREPARATION OF COLOGNE AND HANDKERCHIEF PERFUME

The composition of Example XI is incorporated in a cologne having a concentration of 2.5% in 85% aqueous ethanol; and into a handkerchief perfume in a concentration of 20% (in 95% ethanol). The use of the composition of Example XI affords a distinct and definite "sandal cologne" aroma having a warm sandalwood-like character to the handkerchief perfume and to the cologne.

EXAMPLE XLVII

COLOGNE AND HANDKERCHIEF PERFUME

The 2-methyl-3-methylene-alpha(1-methylethenyl) bicyclo(2.2.1.)heptane-2-exo-propanol produced by the process of Example V(C) in incorporated into a cologne having a concentration of 2.5% in 85% ethanol; and into a handkerchief perfume in a concentration of 10% (in 95% ethanol). The 2-methyl-3-methylene-alpha (1-methylethenyl) bicyclo(2.2.1)heptane-2-exo-propanol produced in Example V(C) affords a distinct and definite sandalwood aroma with warm, woody, sandal odor notes to the handkerchief perfume and to the cologne.

EXAMPLE XLVIII

PREPARATION OF A SOAP COMPOSITION

A total of 100 g of soap chips produced from unperfumed sodium base tiolet soap made from tallow and coconut oil are mixed with 1 g of the perfume composition set forth in Example XII until a substantially homogeneous composition is obtained. The soap composition manifests a characteristic "sandal cologne" aroma having a warm, woody, sandal odor.

EXAMPLE XLIX

PREPARATION OF A SOAP COMPOSITION

A total of 100 g of soap chips produced from unperfumed sodium base toilet soap made from tallow and coconut oil is mixed with 1 g of 2-methyl-3-methylene alpha(1-methylethenyl) bicyclo(2.2.1)heptane 2-endo-propanol until a substantially homogeneous composition is obtained. The soap composition manifests a sandalwood character with oily, green, sandal, woody, peppery, piney aroma with bready, guaicwoody nuances.

EXAMPLE L

PREPARATION OF A DETERGENT COMPOSITION

A total of 100 g of a detergent powder sold under the trademark "RINSO" are mixed with 0.15 g of a perfume composition containing the mixture obtained in Example XII until a substantially homogeneous composition having a "sandal cologne" fragrance with a warm woody, sandal odor is obtained.

EXAMPLE LI

PREPARATION OF A COSMETIC BASE

A cosmetic powder is prepared by mixing 100 g of talcum powder with 0.25 g of the perfume composition of Example XII in a ball mill. A second cosmetic powder is similarly prepared except that the mixture produced in Example XII is replaced with the product produced in Example V(D), 2-methyl-3-methylene alpha (1-methylethenyl) bicyclo(2.2.1)heptane-2-endo-propanol.

The cosmetic powder containing the material of Example XII has a "sandal cologne" fragrance with a warm, woody, sandal odor character. The cosmetic powder produced using this material of Example V(D) has a sandalwood aroma with oily, green, sandal, woody, peppery, piney aroma with bready, guaicwoody nuances.

EXAMPLE LII

LIQUID DETERGENT CONTAINING 2-METHYL-3-METHYLENE ALPHA (1-METHYLETHENYL) BICYCLO(2.2.1)HEPTANE-2-ENDO-PROPANOL

Concentrated liquid detergents with a sandalwood like odor containing 0.2%, 0.5% and 1.2% of the product produced in accordance with the process of Example V(D), 2-methyl-3-methylene alpha(1-methylethenyl) bicyclo(2.2.1)heptane 2-endo-propanol are prepared by adding the appropriate quantity of 2-methyl-3-methylene alpha-(1-methylethenyl) bicyclo(2.2.1-)heptane 2-endo-propanol to the liquid detergent known as P-87. The sandalwood aroma of the liquid detergent increases with increasing concentration of the 2-methyl-3-methylene alpha(1-methylethenyl) bicyclo(2.2.1)heptane 2-endo-propanol of this invention.

EXAMPLE LIII

PREPARATION OF COLOGNE AND HANDKERCHIEF PERFUME

The composition of Example XII is incorporated in a cologne having a concentration of 2.5% in 85% aqueous ethanol; and into a handkerchief perfume in a concentration of 20% (in 95% ethanol). The use of the composition of Example XII affords a distinct and definite "sandal cologne" aroma having a warm sandalwood-like character to the handkerchief perfume and to the cologne.

EXAMPLE LIV

COLOGNE AND HANDKERCHIEF PERFUME

The 2-methyl 3-methylene alpha-(1-methylethenyl) bicyclo(2.2.1)heptane 2-endo-propanol produced by the process of Example V(D) is incorporated into a cologne having a concentration of 2.5% in 85% ethanol; and into a handkerchief perfume in a concentration of 10% (in 95% ethanol). The 2-methyl 3-methylene alpha-(1-methylethenyl) bicyclo(2.2.1)heptane 2-endopropanol produced in Example V(D) affords a distinct and definite sandalwood aroma with warm, woody, sandal odor and oily, green, sandal, woody, peppery, piney aroma with bready, guaicwoody notes to the handkerchief perfume and to the cologne.

EXAMPLE LV

PREPARATION OF A SOAP COMPOSITION

A total of 100 g of soap chips produced from unperfumed sodium base tiolet soap made from tallow and coconut oil are mixed with 1 g of the perfume composition set forth in Example XIII until a substantially homogeneous composition is obtained. The soap composition manifests a characteristic "sandal cologne" aroma having a warm, woody, sandal odor.

EXAMPLE LVI

PREPARATION OF A SOAP COMPOSITION

A total of 100 g of soap chips produced from unperfumed sodium base tiolet soap made from tallow and coconut oil is mixed with 1 g of the mixture of:
i. 5-(2,3-dimethyl tricyclo $(2.2.1.0^{2,6})$ hept-3-yl)-2-methyl-3-penten-2-ol
ii. 5-(2,3-dimethyl tricyclo $(2.2.1.0^{2,6})$ hept-3-yl)-2-methyl-penten-2-ol
iii. 2-methyl-5-(2-exo-methyl-3-methylene-bicyclo-(2.2.1.)-hept-2-yl)-penten-2-ol
iv. 2-methyl-5-(2-exo-methyl-3-methylene-bicyclo-(2.2.1)-hept-2-yl)-penten-2-ol
v. 2-methyl-5-(2-exo-methyl-3-methylene-bicyclo-(2.2.1.)-hept-2-yl)-3-penten-2-ol prepared according to the process of Example I(A) until a substantially homogeneous composition is obtained. The soap composition manifests a sandalwood character.

EXAMPLE LVII

PREPARATION OF A DETERGENT COMPOSITION

A total of 100 g of a detergent powder sold under the trademark "RINSO" are mixed with 0.15 g of a perfume composition containing the mixture obtained in Example XIII until a substantially homogeneous composition having a "sandal cologne" fragrance with a warm, woody, sandal odor is obtained.

EXAMPLE LVIII

PREPARATION OF A COSMETIC BASE

A cosmetic powder is prepared by mixing 100 g of talcum powder with 0.25 g of the perfume composition of Example XIII in a ball mill. A second cosmetic powder is similarly prepared except that the mixture produced in Example XIII is replaced with the column chromatography fractions 23-31 produced in Example I(B) a mixture of:
i. 5-(2,3-dimethyl tricyclo$(2.2.1.0^{2,6})$-hept-3-yl)-2-methyl-3-penten-2-ol
ii. 5-(2,3-dimethyl tricyclo$(2.2.1.0^{2,6})$-hept-3-yl)-2-methyl-penten-2-ol
iii. 2-methyl-5-(2-exo-methyl-3-methylene-bicyclo-(2.2.1)-hept-2-yl)-penten-2-ol
iv. 2-methyl-5-(2-endo-methyl-3-methylene-bicyclo-(2.2.1)-hept-2-yl)-penten-2-ol v. 2-methyl-5-(2-exo-methyl-3-methylene-bicyclo-(2.2.1)-hept-2-yl)-3-penten-2-ol The cosmetic powder containing the material of Example XIII has a "sandal cologne" fragrance with a warm, woody, sandal odor character. The cosmetic powder produced using column chromatography fractions 23–31 of Example I(B) has a sandalwood aroma with almond nuances.

EXAMPLE LIX

LIQUID DETERGENT CONTAINING THE MIXTURE OF: (I) 5-(2,3-DIMETHYL TRICYCLO (2.2.1.0$^{2,6}$)-HEPT-3-YL)-2-METHYL-3-PENTEN-2-OL, (II) 5-(2,3-DIMETHYl TRICYCLO (2.2.1.0$^{2,6}$)-HEPT-3-YL)-2-METHYL-PENTEN-2-OL, (III) 2-METHYL-5-(2-EXO-METHYL-3-METHYLENE-BICYCLO-(2.2.1)-HEPT-2-YL)-PENTEN-2-OL, (IV) 2-METHYL-5-(2-ENDO-METHYL-3-METHYLENE-BICYCLO-(2.2.1)-HEPT-2-YL)-PENTEN-2-OL, (V) 2-METHYL-5-(2-EXO-METHYL-3-METHYLENE-BICYCLO-(2.2.1)-HEPT-2-YL)-3-PENTEN-2-OL

Concentrated liquid detergents with a sandalwood like odor containing 0.2%, 0.5% and 1.2% of the product produced in accordance with the process of Example I(A), the mixture of:
 i. 5-(2,3-dimethyl tricyclo-(2.2.1.0$^{2,6}$)-hept-3-yl)-2-methyl-3-penten-2-ol
 ii. 5-(2,3-dimethyl tricyclo-(2.2.1.0$^{2,6}$)-hept-3-yl)-2-methyl-penten-2-ol
 iii. 2-methyl-5-(2-exo-methyl-3-methylene-bicyclo-(2.2.1)-hept-2-yl)-penten-2-ol
 iv. 2-methyl-5-(2-endo-methyl-3-methylene-bicyclo-(2.2.1)-hept-2-yl)-penten-2-ol
 v. 2-methyl-5-(2-exo-methyl-3-methylene-bicyclo-(2.2.1)-hept-2-yl)-3-penten-2-ol
are prepared by adding the appropriate quantity of the mixture of:
 i. 5-(2,3-dimethyl tricyclo-(2.2.1.0$^{2,6}$)-hept-3-yl)-2-methyl-3-penten-2-ol
 ii. 5-(2,3-dimethyl tricyclo-(2.2.1.0$^{2,6}$)-hept-3-yl)-2-methyl-penten-2-ol
 iii. 2-methyl-5-(2-exo-methyl-3-methylene-bicyclo(2.2.1)-hept-2-yl)-penten-2-ol
 iv. 2-methyl-5-(2-endo-methyl-3-methylene-bicyclo(2.2.1)-hept-2-yl)-penten-2-ol
 v. 2-methyl-5-(2-exo-methyl-3-methylene-bicyclo2.2.1)-hept-2-yl)-3-penten-2-ol
to the liquid detergent known as P-87. The sandalwood aroma of the liquid detergent increases with increasing concentration of the mixture of:
 i. 5-(2,3-dimethyl tricyclo (2.2.1.0$^{2,6}$)-hept-3-yl)-2-methyl-3-penten-2-ol
 ii. 5-(2,3-dimethyl tricyclo (2.2.1.0$^{2,6}$)-hept-3-yl)-2-methyl-penten-2-ol
 iii. 2-methyl-5-(2-exo-methyl-3-methylene-bicyclo(2.2.1)-hept-2-yl)-penten-2-ol
 iv. 2-methyl-5-(2-endo-methyl-3-methylene-bicyclo(2.2.1)-hept-2-yl)-hept-2-yl)-penten-2-ol
 v. 2-methyl-5-(2-exo-methyl-3-methylene-bicyclo(2.2.1)-hept-2-yl)-3-penten-2-ol
of this invention.

EXAMPLE LX

PREPARATION OF COLOGNE AND HANDKERCHIEF PERFUME

The composition of Example XIII is incorporated in a cologne having a concentration of 2.5% in 85% aqueous ethanol, and into a handkerchief perfume in a concentration of 20% (in 95% ethanol). The use of the composition of Example XIII affords a distinct and definite "sandal cologne" aroma having a warm sandalwood-like character to the handkerchief perfume and to the cologne.

EXAMPLE LXI

COLOGNE AND HANDKERCHIEF PERFUME

Column chromatography fractions 23–31 containing a mixture of:
 i. 5-(2,3-dimethyl-tricyclo(2.2.1.0$^{2,6}$)-hept-3-yl)-2-methyl-3-penten-2-ol
 ii. 5-(2,3-dimethyl tricyclo(2.2.1.0$^{2,6}$)-hept-3-yl)-2-methyl-penten-2-ol
 iii. 2-methyl-5-(2-exo-methyl-3-methylene-bicyclo(2.2.1)-hept-2-yl)-penten-2-ol
 iv. 2-methyl-5-(2-endo-methyl-3-methylene-bicyclo(2.2.1)-hept-2-yl)-penten-2-ol
 v. 2-methyl-5-(2-exo-methyl-3-methylene-bicyclo(2.2.1)-hept-2-yl)-3-penten-2-ol
produced by the process of Example I(B) is incorporated into a cologne having a concentration of 2.5% in 85% ethanol; and into a handkerchief perfume in a concentration of 10% (in 95% ethanol). The column chromatography fractions 23–31 which is a mixture of:
 i. 5-(2,3-dimethyl tricyclo-(2.2.1.0$^{2,6}$)-hept-3-yl)-2-methyl-3-penten-2-ol
 ii. 5-(2,3-dimethyl tricyclo(2.2.1.0$^{2,6}$)-hept-3-yl)-2-methyl-penten-2-ol
 iii. 2-methyl-5-(2-exo-methyl-3-methylene-bicyclo-(2.2.1)-hept-2-yl)-3-penten-2-ol
 iv. 2-methyl-5-(2-endo-methyl-3-methylene-bicyclo-(2.2.1)-hept-2-yl)-penten-2-ol
 v. 2-methyl-5-(2-exo-methyl-3-methylene-bicyclo-(2.2.1)-hept-2-yl)-3-penten-2-ol
produced in Example I(B) affords a distinct and definite sandalwood aroms with almond notes to the handkerchief perfume and to the cologne.

EXAMPLE LXII

PREPARATION OF A COSMETIC BASE

A cosmetic powder is prepared by mixing 100 g of talcum powder with 0.25 g of the perfume composition of Example XIII in a ball mill. A second cosmetic powder is similarly prepared except that the mixture produced in Example XIII is replaced with the column chromatography fractions 15–22 produced in Example I(B), a mixture of:
 i. 5-(2,3-dimethyl tricyclo-(2.2.1.0$^{2,6}$)-hept-3-yl)-2-methyl-3-penten-2-ol
 ii. 5-(2,3-dimethyl tricyclo-(2.2.1.0$^{2,6}$)-hept-3-yl)-2-methyl-penten-2-ol
 iii. 2-methyl-5-(2-exo-methyl-3-methylene-bicyclo-(2.2.1)-hept-2-yl)-penten-2-ol
 iv. 2-methyl-5-(2-endo-methyl-3-methylene-bicyclo-(2.2.1)-hept-2-yl)-penten-2-ol
 v. 2-methyl-5-(2-exo-methyl-3-methylene-bicyclo-(2.2.1)-hept-2-yl)-3-penten-2-ol The cosmetic powder containing the material of Example XIII has a "sandal cologne" fragrance with a warm, woody, sandal odor character. The cosmetic powder produced using column chromatography fractions 15–22 of Example I(B) has a sandalwood aroma with an oily nuttiness and acetophenone-like notes.

EXAMPLE LXIII

COLOGNE AND HANDKERCHIEF PERFUME

Column chromatography fractions 15–22 containing a mixture of:
i. 5-(2,3-dimethyl tricyclo-(2.2.1.0$^{2,6}$)-hept-3-yl)-2-methyl-3-penten-2-ol
ii. 5-(2,3-dimethyl tricyclo-(2.2.1.0$^{2,6}$)-hept-3-yl)-2-methyl-penten-2-ol
iii. 2-methyl-5-(2-exo-methyl-3-methylene-bicyclo-(2.2.1)-hept-2-yl)-penten-2-ol
iv. 2-methyl-5-(2-endo-methyl-3-methylene-bicyclo-(2.2.1)-hept-2-yl)-penten-2-ol
v. 2-methyl-5-(2-exo-methyl-3-methylene-bicyclo-(2.2.1)-hept-2-yl)-3-penten-2-ol produced by the process of Example I(B) is incorporated into a cologne having a concentration of 2.5% in 85% ethanol; and into a handkerchief perfume in a concentration of 10% (in 95% ethanol). The column chromatography fractions 15–22 which is a mixture of:
i. 5-(2,3-dimethyl tricyclo(2.2.1.0$^{2,6}$)-hept-3-yl)-2-methyl-3-penten-2-ol
ii. 5-(2,3-dimethyl tricyclo-(2.2.1.0$^{2,6}$)-hept-3-yl)-2-methyl-penten-2-ol
iii. 2-methyl-5-(2-exo-methyl-3-methylene-bicyclo-(2.2.1)-hept-2-yl)-penten-2-ol
iv. 2-methyl-5-(2-endo-methyl-3-methylene-bicyclo-(2.2.1)-hept-2-yl)-penten-2-ol
v. 2-methyl-5-(2-exo-methyl-3-methylene-bicyclo-(2.2.1)-hept-2-yl)-3-penten-2-ol produced in Example I(B) affords a distinct and definite sandalwood aroma with an oily nuttiness and acetophenone-like notes to the handkerchief perfume and to the cologne.

EXAMPLE LXIV

PREPARATION OF A COSMETIC BASE

A cosmetic powder is prepared by mixing 100 g of talcum powder with 0.25 g of the perfume composition of Example XIII in a ball mill. A second cosmetic powder is similarly prepared except that the mixture produced in Example XIII is replaced with the column chromatography fractions 32–38 produced in Example I(B), a mixture of:
i. 5-(2,3-dimethyl tricyclo-(2.2.1.0$^{2,6}$)-hept--3-yl)-2-methyl-3-penten-2-ol
ii. 5-(2,3-dimethyl tricyclo-(2.2.1.0$^{2,6}$)-hept-3-yl)-2-methyl-penten-2-ol
iii. 2-methyl-5-(2-exo-methyl-3-methylene-bicyclo-(2.2.1)-hept-2-yl)-penten-2-ol
iv. 2-methyl-5-(2-endo-methyl-3-methylene-bicyclo-(2.2.1)-hept-2-yl)-penten-2-ol
v. 2-methyl-5-(2-exo-methyl-3-methylene-bicyclo-(2.2.1)-hept-2-yl)-3-penten-2-ol The cosmetic powder containing the material of Example XIII has a "sandal cologne" fragrance with a warm, woody, sandal odor character. The cosmetic powder produced using column chromatography fractions 32–38 of Example I(B) has a sandalwood aroma with leathery nuances.

EXAMPLE LXV

COLOGNE AND HANDKERCHIEF PERFUME

Column chromatography fractions 32–38 containing a mixture of:
i. 5-(2,3-dimethyl tricyclo-(2.2.1.0$^{2,6}$)-hept-3-yl)-2-methyl-3-penten-2-ol
ii. 5-(2,3-dimethyl tricyclo-(2.2.1.0$^{2,6}$)-hept-3-yl)-2-methyl-penten-2-ol
iii. 2-methyl-5-(2-exo-methyl-3-methylene-bicyclo-(2.2.1)-hept-2yl)-penten-2-ol
iv. 2-methyl-5-(2-endo-methyl-3-methylene-bicyclo-(2.2.1)-hept-2-yl)-penten-2-ol
v. 2-methyl-5-(2-exo-methyl-3-methylene-bicyclo-(2.2.1)-hept-2-yl)-3-penten-2-ol produced by the process of Example I(B) is incorporated into a cologne having a concentration of 2.5% in 85% ethanol; and into a handkerchief perfume in a concentration of 10% (in 95% ethanol). The column chromatography fractions 32–38 which is a mixture of:
i. 5-(2,3-dimethyl tricyclo-(2.2.1.0$^{2,6}$)-hept-3-yl)-2-methyl-3-penten-2-ol
ii. 5-(2,3-dimethyl tricyclo-(2.2.1.0$^{2,6}$)-hept-3-yl)-2-methyl-penten-2-ol
iii. 2-methyl-5-(2-exo-methyl-3-methylene-bicyclo-(2.2.1')-hept-2-yl)-penten-2-ol
iv. 2-methyl-5-(2-endo-methyl-3-methylene-bicyclo-(2.2.1)-hept-2-yl)-penten-2-Ol
v. 2-methyl-5-(2-exo-methyl-3-methylene-bicyclo-(2.2.1)-hept-2-yl)-3-penten-2-ol produced in Example I(B) affords a distinct and definite sandalwood aroma with leathery notes to the handkerchief perfume and to the cologne.

EXAMPLE LXVI

SANDAL COLOGNE FORMULATION

The following "Sandal Cologne" perfume formulation is prepared:

| Ingredients | Parts by Weight |
| --- | --- |
| Trimethyl-2,2,3 norbornyl-5)-3 cyclohexanol-1 | 100 |
| 1',2',3',4',5',6',7',8'-octahydro 2',3',8',8'-tetramethyl-2'-acetonaphthone isomer mixture produced according to the process of Example VII of Application for U.S. Letters Patent No. 434,948 filed on January 21, 1974 | 50 |
| 2,5,5-trimethyl acetyl cycloheptane produced according to Example I of U.S. Patent Application 349,180 filed on April 9, 1973 | 10 |
| Eugenol (10% sol. in diethyl phthalate) | 5 |
| Borneol (1% sol. in ethyl alcohol) | 2 |
| Cedrenol (A tricyclic sesquiterpinic aldehyde derived from cedrene, having the structure: | 15 |

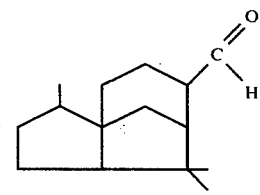

| Ingredients | Parts by Weight |
|---|---|
| produced according to the process of U.S. Patent Application 260,537 filed on June 7, 1972 (corresponding to published Dutch Appl. 7307849 laid open for public inspection on December 11, 1973) | |
| 2,2-dimethyl-3-(2-(2-methyl-3-methylene-bicyclo-(2,2,1)hept-2-(endo)-yl)ethyl)-oxirane having the structure: 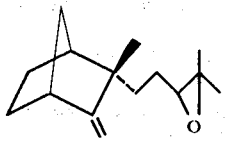 | 50 |

The 2,2-dimethyl-3-(2-(2-methyl-3-methylenebicyclo (2,2,1)hept-2-(endo)-yl)ethyl)-oxirane imparts a green, woody note which is an important odor factor in East Indian Sandalwood.

EXAMPLE LXVII

SANDAL COLOGNE FORMULATION

The following "Sandal Cologne" perfume formulation is prepared:

| Ingredients | Parts by Weight |
|---|---|
| Trimethyl-2,2,3 norbornyl-5)-3 cyclohexanol-1 | 100 |
| 1',2',3',4',5',6',7',8'-octahydro 2',3',8',8'-tetramethyl-2'-aceto-naphthone isomer mixture produced according to the process of Example VII of Application for U.S. Letters Patent No. 434,948 filed on January 21, 1974 | 50 |
| 2,5,5-trimethyl acetyl cycloheptane produced according to Example I of U.S. Patent Application 349,180 filed on April 9, 1973 | 10 |
| Eugenol (10% sol. in diethyl phthalate) | 5 |
| Borneol (1% sol. in ethyl alcohol) | 2 |
| Cedrenal (A tricyclic sesquiterpinic aldehyde derived from cedrene, having the structure: 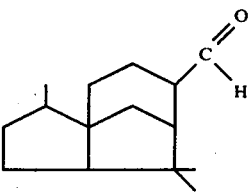 produced according to the process of U.S. Patent Application 260,537 filed on June 7, 1972 (corresponding to published Dutch Appl. 7307849 laid open for public inspection on December 11, 1973) | |
| 2,2-dimethyl-3-(2-(2-methyl-3-methylenebicyclo(2,2,1)hept-2-(exo)-yl)ethyl)-oxirane having the following structure: 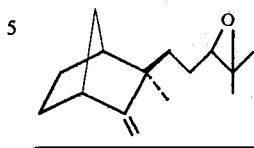 | 50 |

The 2,2-dimethyl-3-(2-(2-methyl-3-methylenebicyclo (2,2,1)hept-2(exo)-yl)ethyl)-oxirane imparts a green, woody note which is an important order factor in East Indian Sandalwood.

EXAMPLE LXVIII

SANDAL COLOGNE FORMULATION

The following "Sandal Cologne" perfume formulation is prepared:

| Ingredients | Parts by Weight |
|---|---|
| Trimethyl-2,2,3-norbornyl-5)-3 cyclohexanol-1 | 100 |
| 1',2',3',5',6',7',8'-octahydro 2',3',8',8'-tetramethyl-2'-aceto-naphthone isomer mixture produced according to the process of Example VII of Application for U.S. Letters Patent No. 434,948 filed on January 21, 1974 | 50 |
| 2,5,5-trimethyl acetyl cycloheptane produced according to Example I of U.S. Patent Application 349,180 filed on April 9, 1973 | 10 |
| Eugenol (10% sol. in diethyl phthalate) | 5 |
| Borneol (1% sol. in ethyl alcohol) | 2 |
| Cedrenal (A tricyclic sesquiterpinic aldehyde derived from cedrene, having the structure: 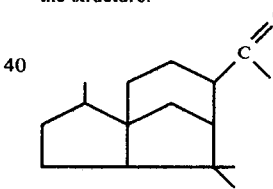 produced according to the process of U.S. Patent Application 260,537 filed on June 7, 1972 (corresponding to published Dutch appl. 7307849 laid open for public inspection on December 11, 1973). | |
| Mixture of 2,2-dimethyl-3-(2-(2,3-dimethyl tricyclo(2,2,1,0$^{2,6}$)hept-3-yl)ethyl-oxirane; 2,2-dimethyl-3-(2-(2-methyl-3-methylene bicyclo(2,2,1)hept-2-(endo)-yl)ethyl)-oxirane; 2,2-dimethyl-3-(2-(2-methyl-3-methylene bicyclo(2,2,1)hept-2(exo)-yl)ethyl)-oxirane | 50 |

The mixture of 2,2-dimethyl-3-(2-(2,3-dimethyltricyclo(2,2,1,0$^{2,6}$)hept-3-yl)ethyl-oxirane; 2,2-dimethyl-3-(2-(2-methyl-3-methylene bicyclo(2,2,1) hept-2-(endo)-yl)ethyl)-oxirane; 2,2-dimethyl-3-(2-(2-methyl-3-methylene bicyclo(2,2,1)hept-2-(exo)-yl)ethyl)-oxirane imparts a green, woody note which is an important odor factor in East Indian Sandalwood.

EXAMPLE LXIX

SANDAL PERFUME FORMULATION

The following mixture is prepared:

| Ingredients | Parts by Weight |
|---|---|
| Cedrenal (A tricyclic sesquiterpinic aldehyde derived from cedrene, having the structure: | 100 |

[structure: tricyclic sesquiterpenic aldehyde with -C(=O)H group]

produced according to the process of U.S. Patent Application 260,537 filed on June 7, 1972 (corresponding to published Dutch Appl. 7307849 laid open for public inspection on December 11, 1973).

| | |
|---|---|
| Cedrenol | 25 |
| 2,5,5-trimethyl acetyl cycloheptane produced according to Example 1 of U.S. Patent Application 349,180 filed on April 9, 1973 | 10 |
| 5,6-epoxy-2,6,10,10-tetramethyl bicyclo (7.2.0) undecane | 30 |
| Eugenol (10% sol. in diethyl phthalate) | 10 |
| Borneol (1% sol. in ethyl alcohol) | 3 |
| Alpha, alpha,2,3-tetramethyl-tricyclo (2.2.1.0$^{2.6}$)heptane-3-butanol, having the structure: | 100 |

[structure with OH group]

The alpha,alpha,2,3-tetramethyl-tricyclo(2.2.1.0$^{2.6}$)heptane-3-butanol imparts a green, woody note which is an important note in East Indian Sandalwood.

EXAMPLE LXX

SANDAL PERFUME FORMULATION

The following mixture is prepared:

| Ingredients | Parts by Weight |
|---|---|
| Cedrenal (A tricyclic sesquiterpinic aldehyde derived from cedrene, having the structure: | 100 |

[structure: tricyclic sesquiterpenic aldehyde with -C(=O)H group]

produced according to the process of U.S. Patent Application 260,537 filed on June 7, 1972 (corresponding to published Dutch appl. 7307849 laid open for public inspection on December 11, 1973).

| | |
|---|---|
| Cedrenol | 25 |
| 2,5,5-trimethyl acetyl cycloheptane produced according to Example 1 of U.S. Patent Application 349,180 filed on April 9, 1973 | 10 |
| 5,6-epoxy-2,6,10,10-tetramethyl bicyclo (7.2.0) undecane | 30 |
| Eugenol (10% sol. in diethyl phthalate) | 10 |
| Borneol (1% sol. in ethyl alcohol) | 3 |
| alpha, alpha, 2-trimethyl-3-methylene-bicyclo(2.2.1)heptane-2-endo-butanol having the structure: | 100 |

[structure with OH group]

The alpha, alpha, 2-trimethyl-3-methylenebicyclo(2.2.1)heptane-2-endo-butanol imparts a green, woody note which is an important note in East Indian Sandalwood.

EXAMPLE LXXI

SANDAL PERFUME FORMULATION

The following mixture is prepared:

| Ingredients | Parts by Weight |
|---|---|
| Cedrenal (A tricyclic sesquiterpinic aldehyde derived from cedrene, having the structure: | 100 |

[structure: tricyclic sesquiterpenic aldehyde with -C(=O)H group]

produced according to the process of U.S. Patent Application 260,537 filed on June 7, 1972 (corresponding to published Dutch Appl. 7307849 laid open for public inspection on December 11, 1973)

| | |
|---|---|
| Cedrenol | 25 |
| 2,5,5-trimethyl acetyl cycloheptane produced according to Example 1 of U.S. Patent Application 349,180 filed on April 9, 1973 | 10 |
| 5,6-epoxy-2,6,10,10-tetramethyl bicyclo(7.2.0) undecane | 30 |
| Eugenol (10% sol. in diethyl phthalate) | 10 |
| Borneol (1% sol. in diethyl alcohol) | 3 |
| alpha, alpha, 2-trimethyl-3-methylene bicyclo(2.2.1)heptane-2(exo)-butanol having the structure: | 100 |

-continued

| Ingredients | Parts by Weight |
|---|---|
| 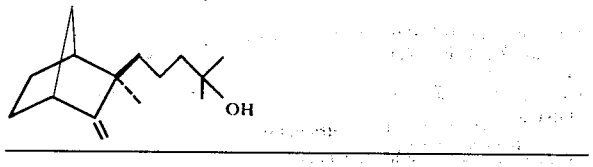 | |

The alpha, alpha, 2-trimethyl-3-methylene-bicyclo-(2.2.1)heptane-2(exo)-butanol imparts a green, woody note which is an important note in East Indian Sandalwood.

EXAMPLE LXXII

SANDAL PERFUME FORMULATION

The following mixture is prepared:

| Ingredients | Parts by Weight |
|---|---|
| Cedrenal (A tricyclic sesquiterpinic aldehyde derived from cedrene, having the structure: 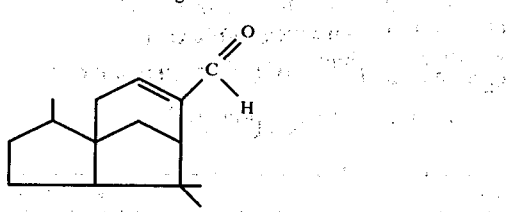 produced according to the process of U.S. Patent Application 260,537 filed on June 7, 1972 (corresponding to published Dutch Appl. 7307849 laid open for public inspection on December 11, 1973) | 100 |
| Cedrenol | 25 |
| 2,5,5-trimethyl acetyl cycloheptane produced according to Example I of U.S. Patent Application 349,180 filed on April 9, 1973 | 10 |
| 5,6-epoxy-2,6,10,10-tetramethyl bicyclo (7.2.0) undecane | 30 |
| Eugenol (10% sol. in diethyl phthalate) | 10 |
| Borneol (1% sol. in ethyl alcohol) | 3 |
| Mixture of alpha, alpha, 2,3-tetra-methyl-tricyclo-(2.2.1.0²,⁶)heptane-3-butanol; alpha, alpha, 2-trimethyl-3-methylene bicyclo(2.2.1)heptane-2-endo-butanol; alpha, alpha, 2-trimethyl-3-methylene bicyclo(2.2.1)heptane-2(exo)-butanol | 100 |

The mixture of alpha, alpha, 2,3-tetramethyltricyclo(2.2.1.0²,⁶)heptane-3-butanol; alpha, alpha, 2-trimethyl-3-methylene bicyclo(2.2.1)heptane-2-endobutanol; alpha, alpha, 2-trimethyl-3-methylene bicyclo (2.2.1)heptane-2(exo)-butanol imparts a green, woody note which is an important note in East Indian Sandalwood.

Want is claimed is:

1. A process for the preparation of at least one compound having a structure selected from the group consisting of:

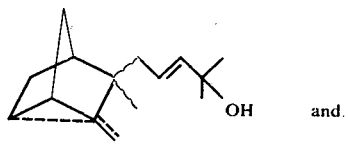 and

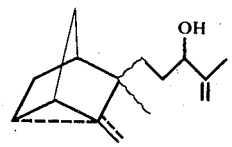

wherein one of the dashed lines is a carbon-carbon bond and each of the wavy lines is a carbon-carbon single bond, one of the carbon-carbon single bonds represented by the wavy line being epimeric with respect to the other of the carbon-carbon single bonds represented by the wavy line, comprising the steps of:
  i. Subjecting one or more hydrocarbon compounds represented by the structure:

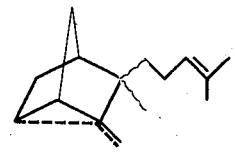

to an intense, oxidation step which comprises continuously insufflating air through said hydrocarbon compound, while agitating said hydrocarbon compound, and exposing said hydrocarbon compound to ultra violet light in the presence of a catalyst comprising an alkali metal hydroxide and rose bengal and an inert solvent at a temperature in the range of from 15° C up to 40° C; and
  ii. Fractionally distilling the resulting reaction products.

2. The process of claim 1, wherein the hydrocarbon subjected to the intense oxidation step has the structure:

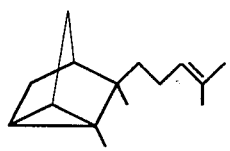

and the reaction product consists essentially of compounds having the structures:

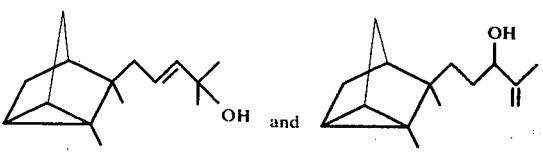

3. The process of claim 1, wherein the hydrocarbon subjected to the intense oxidation step has the structure:

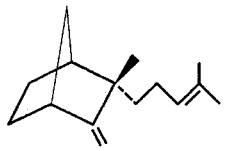

and the reaction product consists essentially of compounds having the structures:

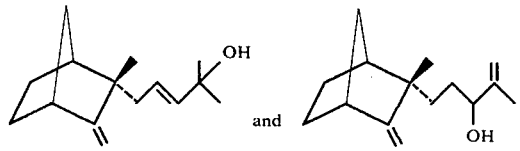

4. The process of claim 1, wherein the hydrocarbon subjected to the intense oxidation step has the structure:

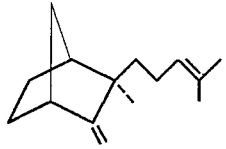

and the reaction product consists essentially of compounds having the structures:

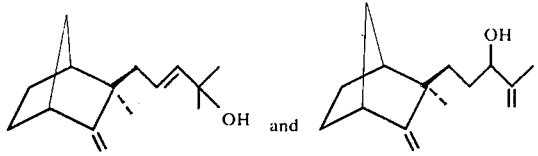

5. The process of claim 1, wherein the solvent used during the oxidation step is a mixture of methanol and benzene.

6. The process of claim 1, wherein the weight ratio of alkali metal hydroxide:rose bengal is 5:2.

7. The process of claim 1 wherein the hydrocarbon compounds represented by the generic structure:

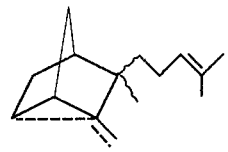

are produced in admixture with one another by means of distillation of saponified sandalwood oil.

8. The process of claim 1 wherein the hydrocarbons represented by the generic structure:

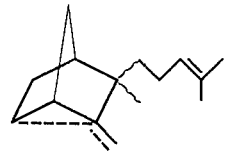

are produced in admixture with one another by the steps of:
 a. admixing sandalwood oil with a lower alkanol and sodium hydroxide;
 b. removing the lower alkanol from the resulting mixture;
 c. admixing the resulting a mixture with an acid whereby the pH of the mixture is reduced to 5.5;
 d. washing the resulting mixture with water whereby the pH of the resulting mixture is increased to 7; and
 e. fractionally distilling the resulting mixture.

* * * * *